US009773491B2

(12) United States Patent
Ku et al.

(10) Patent No.: US 9,773,491 B2
(45) Date of Patent: Sep. 26, 2017

(54) ESTIMATING SECONDARY PATH MAGNITUDE IN ACTIVE NOISE CONTROL

(71) Applicant: Bose Corporation, Framingham, MA (US)

(72) Inventors: Emery Ku, Somerville, MA (US); Paraskevas Argyropoulos, Everett, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 14/856,062

(22) Filed: Sep. 16, 2015

(65) Prior Publication Data

US 2017/0076709 A1 Mar. 16, 2017

(51) Int. Cl.

*A61F 11/06* (2006.01)
*G10K 11/16* (2006.01)
*G10K 11/178* (2006.01)

(52) U.S. Cl.

CPC ........ *G10K 11/178* (2013.01); *G10K 11/1786* (2013.01); *G10K 2210/1282* (2013.01); *G10K 2210/3028* (2013.01); *G10K 2210/3055* (2013.01); *G10K 2210/30232* (2013.01)

(58) Field of Classification Search

CPC ... G10K 2210/3028; G10K 2210/3017; G10K 2210/3045; G10K 2210/3055; G10K 2210/3056; G10K 11/178; G10K 11/1782; G10K 11/1784; G10K 2210/1282; G10K 2210/12822

USPC ......... 381/71.1, 71.2, 71.3, 71.4, 71.5, 71.6, 381/71.7, 71.8, 94.1, 97

See application file for complete search history.

(56) References Cited

U.S. PATENT DOCUMENTS 5,689,572 A 11/1997 Ohki et al.
6,201,872 B1 3/2001 Hersh et al.

(Continued)

FOREIGN PATENT DOCUMENTS

EP 0 721 179 7/1996

OTHER PUBLICATIONS

Gay et al.; "The Fast Affine Projection Algorithm"; Acoustics Research Department, At&T Bell Laboratories; 1995; 4 pp.

Glover, Jr.; "Adaptive Noise Canceling Applied to Sinusoidal Interferences"; IEE Transactions on Acoustics, Speech and Signal Procesisng; vol. ASSP-25; No. 6; Dec. 1977; 8 pp.

(Continued)

*Primary Examiner* — William A Jerez Lora
(74) *Attorney, Agent, or Firm* — Fish & Richardson P.C.

(57) ABSTRACT

The technology described in this document can be embodied in a computer-implemented method that includes receiving a first plurality of values representing a set of current coefficients of an adaptive filter disposed in an active noise cancellation system. The method also includes computing a second plurality of values each of which represents an instantaneous difference between a current coefficient and a corresponding preceding coefficient of the adaptive filter, and estimating, based on the second plurality of values, one or more instantaneous magnitudes of a transfer function that represents an effect of a secondary path of the active noise cancellation system. The method further includes updating the first plurality of values based on estimates of the one or more instantaneous magnitudes to generate a set of updated coefficients for the adaptive filter, and programming the adaptive filter with the set of updated coefficients.

20 Claims, 17 Drawing Sheets

(56) References Cited

U.S. PATENT DOCUMENTS

| | | | | |
|---|---|---|---|---|
| 6,449,368 | B1 * | 9/2002 | Davis | H04S 1/002 381/1 |
| 8,744,093 | B2 | 6/2014 | Sakamoto et al. | |
| 9,230,535 | B2 | 1/2016 | Yano | |
| 9,240,819 | B1 | 1/2016 | Ku | |
| 2004/0264706 | A1 * | 12/2004 | Ray | G10K 11/178 381/71.11 |
| 2011/0249826 | A1 | 10/2011 | Van Leest | |
| 2013/0044891 | A1 | 2/2013 | Obata et al. | |
| 2013/0301842 | A1 * | 11/2013 | Hendrix | G10K 11/002 381/71.1 |
| 2015/0010164 | A1 | 1/2015 | Christoph | |
| 2015/0071453 | A1 | 3/2015 | Po et al. | |
| 2016/0042731 | A1 | 2/2016 | Chang | |
| 2016/0314778 | A1 * | 10/2016 | Christoph | G10K 11/1786 |

OTHER PUBLICATIONS

Kuo et al.; "Active Noise Control: A Tutorial Review"; Proceedings of the IEEE, vol. 87, No. 6, Jun. 1999; 31 pp.

Sayyarrodsari, et al.; "An Hoo—Optimal Alternative to the FxLMS Algorithm"; AACC; 1998; 6 pp.

U.S. Appl. No. 14/855,961, filed Sep. 16, 2015, Estimated Secondary Path Phase in Active Noise Control.

International Search Report and Written Opinion; PCT/US2016/048851; Nov. 15, 2016; 10 pages.

International Search Report and Written Opinion; PCT/US2016/048841; Dec. 5, 2016; 12 pages.

Lee, et al.; "An Active Noise Control Algorithm for Controlling Multiple Sinusoids"; The Journal of the Acoustical Society of America: vol. 104, No. 1, N.p., Mar. 25, 1998.

* cited by examiner

ESTIMATING SECONDARY PATH MAGNITUDE IN ACTIVE NOISE CONTROL

TECHNICAL FIELD

This disclosure generally relates to active noise control.

BACKGROUND

Active noise control involves cancelling unwanted noise by generating a substantially opposite signal often referred to as anti-noise.

SUMMARY

In one aspect, this document features a computer-implemented method that includes receiving, at one or more processing devices, a first plurality of values representing a set of current coefficients of an adaptive filter disposed in an active noise cancellation system. The method also includes computing, by the one or more processing devices, a second plurality of values each of which represents an instantaneous difference between a current coefficient and a corresponding preceding coefficient of the adaptive filter, and estimating, based on the second plurality of values, one or more instantaneous magnitudes of a transfer function that represents an effect of a secondary path of the active noise cancellation system. The method further includes updating the first plurality of values based on estimates of the one or more instantaneous magnitudes to generate a set of updated coefficients for the adaptive filter, and programming the adaptive filter with the set of updated coefficients to affect operation of the adaptive filter.

In another aspect, this document features an active noise control engine that includes one or more processing devices. The active noise control engine can be configured to receive a first plurality of values representing a set of current coefficients of an adaptive filter disposed in an active noise cancellation system. The active noise control engine is also configured to compute a second plurality of values each of which represents an instantaneous difference between a current coefficient and a corresponding preceding coefficient of the adaptive filter, and estimate, based on the second plurality of values, one or more instantaneous magnitudes of a transfer function that represents an effect of a secondary path of the active noise cancellation system. The active noise control engine is further configured to update the first plurality of values based on estimates of the one or more instantaneous magnitudes to generate a set of updated coefficients for the adaptive filter, and program the adaptive filter with the set of updated coefficients to affect operation of the adaptive filter.

In another aspect, this document features one or more machine-readable storage devices having encoded thereon computer readable instructions for causing one or more processors to perform various operations. The operations include receiving a first plurality of values representing a set of current coefficients of an adaptive filter disposed in an active noise cancellation system. The operations also include computing a second plurality of values each of which represents an instantaneous difference between a current coefficient and a corresponding preceding coefficient of the adaptive filter, and estimating, based on the second plurality of values, one or more instantaneous magnitudes of a transfer function that represents an effect of a secondary path of the active noise cancellation system. The operations further include updating the first plurality of values based on estimates of the one or more instantaneous magnitudes to generate a set of updated coefficients for the adaptive filter, and programming the adaptive filter with the set of updated coefficients to affect operation of the adaptive filter.

Implementations of the above aspects can include one or more of the following features.

The one or more instantaneous magnitudes can be estimated based on a rate at which the coefficients of the adaptive filter change over time. Determining the one or more instantaneous magnitudes of the transfer function can include applying a digital filter on the second plurality of values, and determining the one or more instantaneous magnitudes of the transfer function based on an output of the digital filter. Estimating one or more instantaneous magnitudes of the transfer function can further include determining a reciprocal of a value of the rate at which the coefficients of the adaptive filter change over time, and estimating the one or more instantaneous magnitudes of the transfer function based on the reciprocal of the value of the rate. One or more estimates of instantaneous phase values associated with the transfer function can be received at the processing devices, and the first plurality of values can be updated based also on the one or more estimates of instantaneous phase values. The one or more estimates of instantaneous phase values can be generated analytically during an operation of the adaptive filter, and independent of any prior model of the secondary path. The one or more estimates of instantaneous phase values can be generated using an unsupervised learning process. A control signal can be generated based on an output of the adaptive filter, wherein the control signal causes production of an anti-noise signal configured to reduce the effect of a noise signal. The noise signal can be generated by a vehicle engine. The first plurality of values can be updated based also on an error signal produced based on residual noise resulting from at least a partial cancellation of the noise signal by the anti-noise signal. The active noise cancellation system can include one or more acoustic transducers for generating an anti-noise signal for canceling a noise signal, and one or more microphones for sensing a residual noise resulting from at least a partial cancellation of the noise signal by the anti-noise signal. The transfer function can be represented as a matrix, wherein a given element of the matrix represents a secondary path between a particular microphone of the one or more microphones and a particular acoustic transducer of the one or more acoustic transducers.

Various implementations described herein may provide one or more of the following advantages. By using technology described herein, an adaptive filter can be configured to account for phase and/or magnitude changes in one or more secondary path transfer functions of an active noise cancellation (ANC) system. In some implementations, the filter can be made adaptive with respect to both phase and magnitude changes in the one or more secondary path transfer functions, which in turn may improve accuracy and convergence speed of the adaptive filter. In some cases, this may be done without making any measurements to model the secondary paths. In certain cases, this may lead to savings in production time and/or cost for the ANC system. For example, the technology described in this document may obviate or reduce the need for time-consuming measurements which may be needed for modeling secondary paths associated with ANC systems deployed in vehicles. This may be particularly advantageous for vehicles in pre-production stages, when procuring the vehicles for a time sufficient to perform measurements is often challenging and/or expensive. By allowing for an adaptive and run-time characterization of one or more secondary path transfer functions, ANC systems may be made self-tuning with respect to dynamic changes of the environment. (e.g., in a vehicle, where rolling down of a window or placing a large item inside the cabin may affect the acoustic environment).

Two or more of the features described in this disclosure, including those described in this summary section, may be combined to form implementations not specifically described herein.

The details of one or more implementations are set forth in the accompanying drawings and the description below. Other features, objects, and advantages will be apparent from the description and drawings, and from the claims.

DETAILED DESCRIPTION

The present application describes techniques for implementing active noise control (ANC) systems.

Active noise control systems are used for cancelling or reducing unwanted or unpleasant noise produced by equipment such as engines, blowers, fans, transformers, and compressors. Active noise control can also be used in automotive or other transportation systems (e.g., in cars, trucks, buses, aircrafts, boats or other vehicles) to cancel or attenuate unwanted noise produced by, for example, mechanical vibrations or engine harmonics.

In some cases, Active Noise Control (ANC) systems can be used for attenuating or canceling unwanted noise. In some cases, an ANC system can include an electroacoustic or electromechanical system that can be configured to cancel at least some of the unwanted noise (often referred to as primary noise) based on the principle of superposition. This can be done by identifying an amplitude and phase of the primary noise and producing another signal (often referred to as an anti-noise) of about equal amplitude and opposite phase. An appropriate anti-noise combines with the primary noise such that both are substantially canceled (e.g., canceled to within a specification or acceptable tolerance). In this regard, in the example implementations described herein, "canceling" noise may include reducing the "canceled" noise to a specified level or to within an acceptable tolerance, and does not require complete cancellation of all noise. ANC systems can be used in attenuating a wide range of noise signals, including low-frequency noise that may not be easily attenuated using passive noise control systems. In some cases, ANC systems provide feasible noise control mechanisms in terms of size, weight, volume, and cost.

Figure 1:
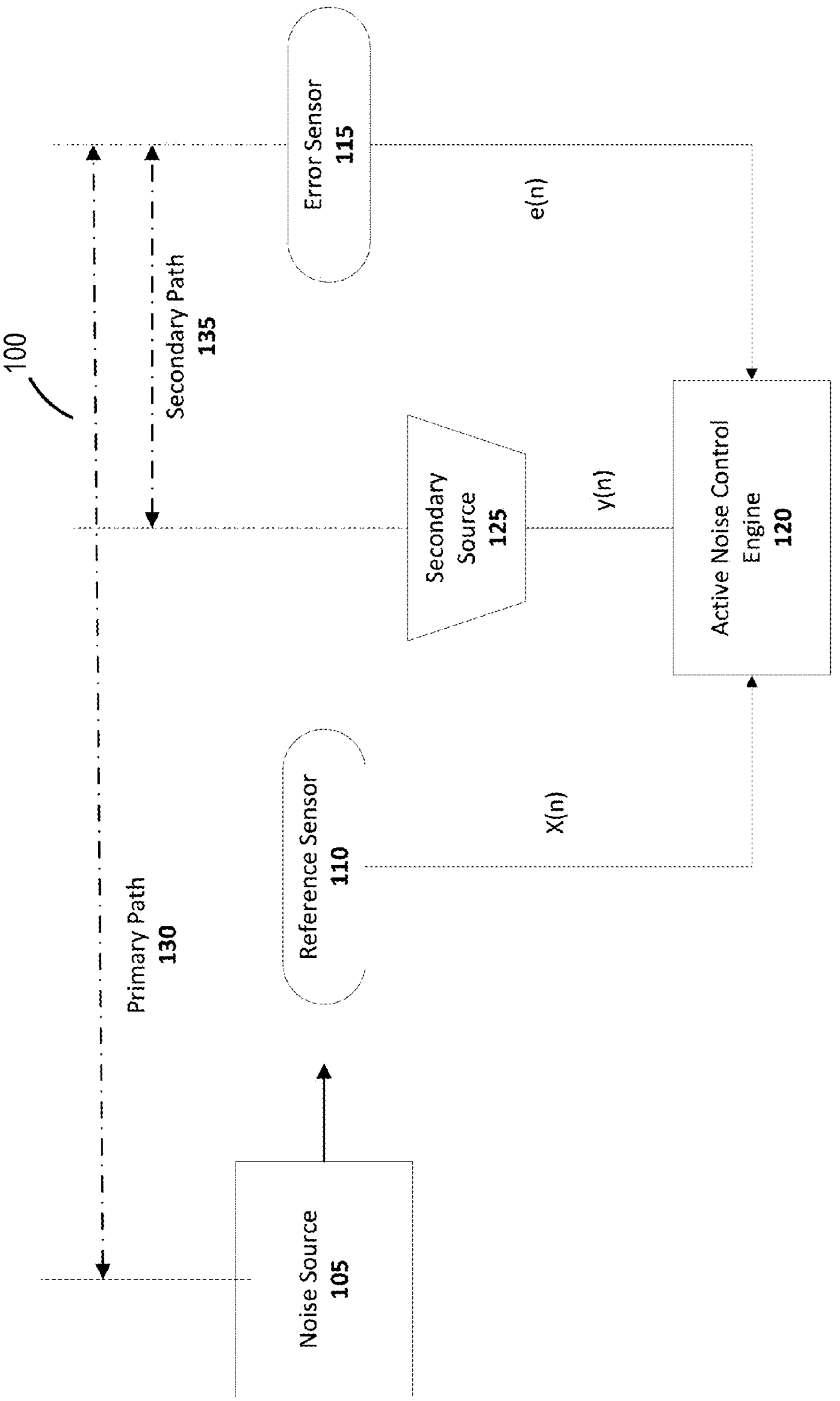
FIG. 1 is a diagram showing an example of an active noise control (ANC) system.

FIG. 1 shows an example of an active noise control system 100 for canceling a noise produced by a noise source 105. This noise can be referred to as the primary noise. The system 100 includes a reference sensor 110 that detects the noise from the noise source 105 and provides a signal to an ANC engine 120 (e.g., as a digital signal x(n)). The ANC engine 120 produces an anti-noise signal (e.g., as a digital signal y(n)) that is provided to a secondary source 125. The secondary source 125 produces a signal that cancels or reduces the effect of the primary noise. For example, when the primary noise is an acoustic signal, the secondary source 125 can be configured to produce an acoustic anti-noise that cancels or reduces the effect of the acoustic primary noise. Any cancellation error can be detected by an error sensor 115. The error sensor 115 provides a signal (e.g., as a digital signal e(n)) to the ANC engine 120 such that the ANC engine can modify the anti-noise producing process accordingly to reduce or eliminate the error.

Components between the noise source 105 and the error sensor 115 are often collectively referred to as the primary path 130, and components between the secondary source 125 and error sensor 115 are often collectively referred to as the secondary path 135. For example, in ANC systems for cancelling acoustic noise, the primary path can include an acoustic distance between the noise source and an error sensing microphone, and the secondary path can include an acoustic distance between an acoustic anti-noise producing speaker and an error sensing microphone. The primary path 130 and/or the secondary path 135 can also include additional components such as components of the ANC system or the environment in which the ANC system is deployed. For example, the secondary path can include one or more components of the ANC engine 120, secondary source 125, and/or the error sensor 115. In some implementations, the secondary path can include electronic components of the ANC engine 120 and/or the secondary source 125, such as one or more digital filters, amplifiers, digital to analog (D/A) converters, analog to digital (A/D) converters, and digital signal processors. In some implementations, the secondary path can also include an electro-acoustic response associated with the secondary source 125, an acoustic path associated with the secondary source 125 and dynamics associated with the error sensor 115. Dynamic changes to one or more of the above components can affect the model of the secondary path, which in turn may affect the performance of the ANC system.

The ANC engine 120 can include an adaptive filter, the coefficients of which can be adaptively changed based on variations in the primary noise. The variations of the filter coefficients may be represented in an N-dimensional space, where N is the number of coefficients associated with the adaptive filter. For example, coefficient variation of a two-tap filter (e.g., a filter with two coefficients) can be represented on a two-dimensional plane. The time-varying path of the filter coefficients in the corresponding space can be referred to as the filter coefficient trajectory associated with the adaptive filter. The time-varying coefficients of the adaptive filter can be generated, for example, based on a transfer function associated with the adaptive filter. The transfer function can be generated based on the characteristics of the secondary path, which, in some cases, do not vary with time. In some situations however, the electro-acoustic characteristics of the secondary path 135 can vary as a function of time. The example implementations described in this document allow for dynamically updating the model of the secondary path 135 based on the filter coefficient trajectory, thereby leading to cancellation of at least a portion of the noise.

The noise source 105 can be of various types. For example, the noise source 105 can be a vehicular engine associated with a car, an aircraft, a ship or boat, or a railway locomotive. In some implementations, the noise source 105 can include an appliance such as a heating, ventilation, and air conditioning (HVAC) system, a refrigerator, an exhaust fan, a washing machine, a lawn mower, a vacuum cleaner, a humidifier, or a dehumidifier. The noise source 105 can also include industrial noise sources such as industrial fans, air ducts, chimneys, transformers, power generators, blowers, compressors, pumps, chain saws, wind tunnels, noisy plants or offices. Correspondingly, the primary path 130 includes the acoustic path between the noise source 105 and the location where the reference sensor 110 is disposed. For example, to reduce noise due to a HVAC system, the reference sensor 110 can be disposed within an air duct to detect the corresponding primary noise. The primary noise generated by the noise source 105 can include harmonic noise.

The reference sensor 110 can be selected based on the type of primary noise. For example, when the primary noise is acoustic, the reference sensor 110 can be a microphone. In implementations where the primary noise is produced by sources other than an acoustic source, the reference sensor 110 can be selected accordingly. For example, when the primary noise is harmonic noise from an engine, the reference sensor 110 can be a tachometer. The example ANC technology described in the document may therefore be applied for cancelling or reducing the effect of different types of noises using appropriate reference sensors 110 and secondary sources. For example, to control a structural vibration, the reference sensor 110 can be a motion sensor (e.g., an accelerometer) or a piezoelectric sensor and the secondary source 125 can be a mechanical actuator that can be configured to produce an appropriate vibratory anti-noise.

Figure 2:
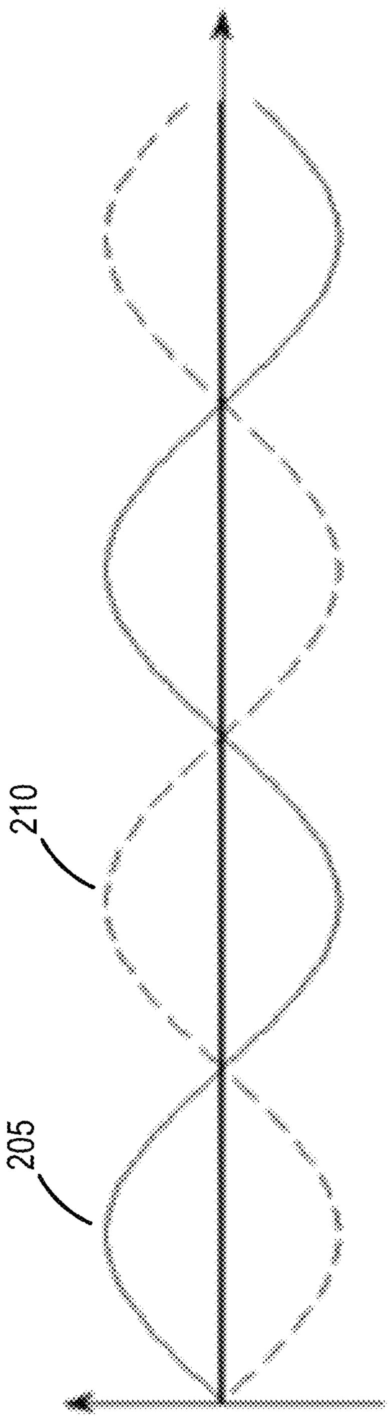
FIG. 2 is a plot illustrating principles of an ANC system.

In some implementations, the secondary source 125 can be positioned such that the acoustic signal produced by the secondary source 125 reduces the effect of the primary noise. For example, if the system 100 is deployed to reduce the effect of engine noise within the cabin of a car, the secondary source 125 is deployed within the cabin. In this example, the secondary source 125 is configured to produce an acoustic signal that cancels or reduces the effect of primary noise within a target environment. This is illustrated with the example shown in FIG. 2. In FIG. 2, the goal is to cancel or reduce the effect of the acoustic signal represented by the wave 205. In such a case, the secondary source 125 can be configured to produce an acoustic signal represented by the wave 210 to cancel or reduce the effect of the signal represented by the wave 205. The amplitude and phase of the signal represented by the wave 210 can be configured such that a superposition of the two signals effectively cancel the effect of one another. Note that acoustic signals are longitudinal waves, and represented using the transverse waves 205 and 210 for illustrative purposes.

In some cases, the characteristics of the primary noise may vary with time. In such cases, the acoustic signal generated by the secondary source 125 may not immediately reduce the primary noise to a desirable level. In some cases, this can give rise to a residual noise that is detected by the error sensor 115. Accordingly, the error sensor 115 provides a signal (e.g., the digital signal e(n)) to the ANC engine 120, which adjusts the output (e.g., y(n)) provided to the secondary source in a way that the residual noise is reduced. The error sensor 115 is therefore deployed in the target environment in some implementations. For example, when the ANC system is deployed for reducing engine noise within the cabin of a car, the error sensor 115 can be deployed within the cabin in a position where it would effectively detect residual noise.

The ANC engine 120 can be configured to process the signals detected by the reference sensor 110 and the error sensor 115 to produce a signal that is provided to the secondary source 125. The ANC engine 120 can be of various types. In some implementations, the ANC engine 120 is based on feed-forward control, in which the primary noise is sensed by the reference sensor 110 before the noise reaches the secondary source such as the secondary source 125. In some implementations, the ANC engine 120 can be based on feedback control, where the ANC engine 120 attempts to cancel the primary noise based on the residual noise detected by the error sensor 115 and without the benefit of a reference sensor 110.

The ANC engine 120 can be configured to control noise in various frequency bands. In some implementations, the ANC engine 120 can be configured to control broadband noise such as white noise. In some implementations, the ANC engine 120 can be configured to control narrow band noise such as harmonic noise from a vehicle engine. In some implementations, the ANC engine 120 includes an adaptive digital filter, the coefficients of which can be adjusted based on, for example, the variations in the primary noise. In some implementations, the ANC engine is a digital system, where signals from the reference and error sensors (e.g., electroacoustic or electromechanical transducers) are sampled and processed using processing devices such as digital signal processors (DSP), microcontrollers or microprocessors. Such processing devices can be used to implement adaptive signal processing processes used by the ANC engine 120.

Figure 3:
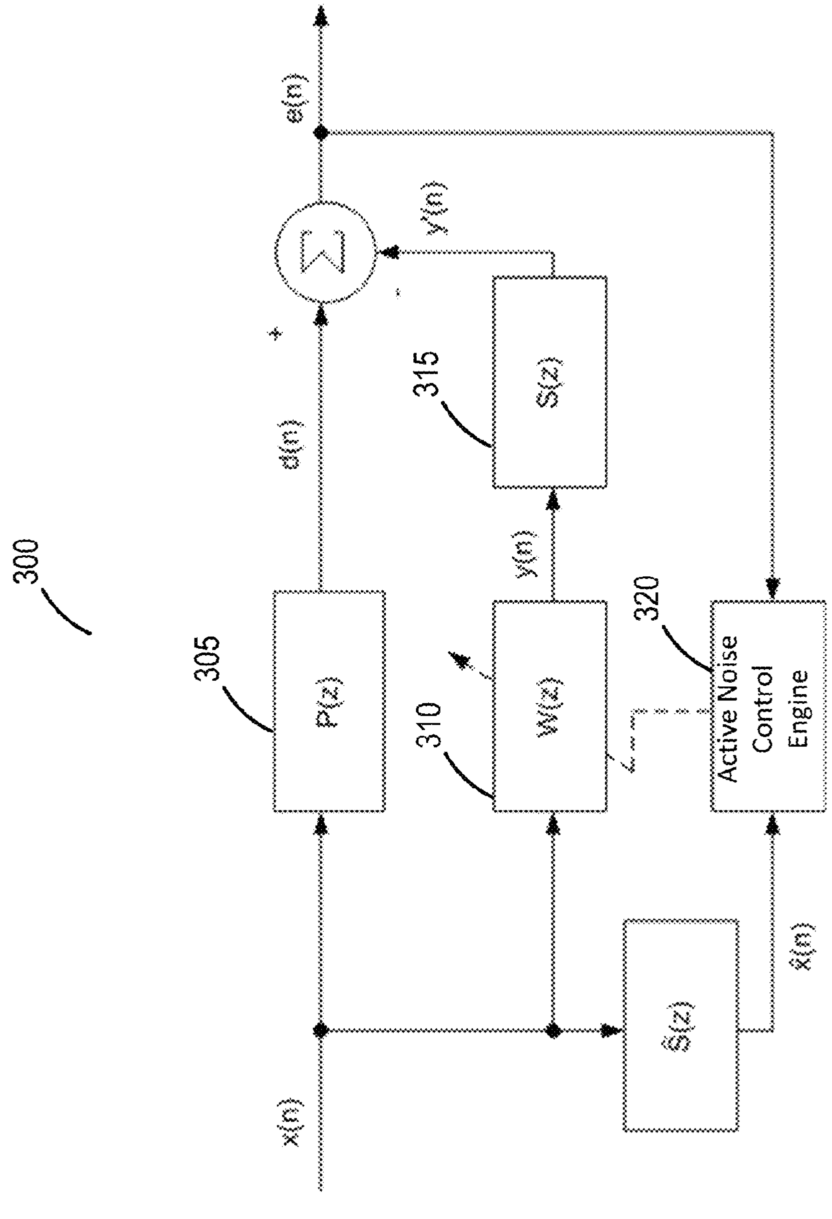
FIG. 3 is a block diagram of an example ANC system.

FIG. 3 is a block diagram showing implementation details of an example ANC system 300. The ANC system 300 includes an adaptive filter that adapts to an unknown environment 305 represented by P(z) in the z domain. In this document, frequency domain functions may be represented in terms of their z domain representations, with the corresponding time domain (or sample domain) representations being functions of n. In the present example, the primary path includes an acoustic path between the reference sensor and the error sensor. Also, in this example, the transfer function of the secondary path 315 is represented as S(z). The adaptive filter 310 (represented as W(z)) can be configured to track time variations of the environment 305. In some implementations, the adaptive filter 310 can be configured to reduce (e.g., to substantially minimize) the residual error signal e(n). Therefore, the adaptive filter 310 is configured such that the target output y(n) of the adaptive filter 310, as processed by the secondary path, is substantially equal to the primary noise d(n). The output, when processed by the secondary path, can be represented as y'(n). The primary noise d(n), in this example is the source signal x(n) as processed by the unknown environment 305. Comparing FIG. 3 with the example of an ANC system 100 deployed in a car, the secondary path 315 can therefore include the secondary source 125 and/or the acoustic path between the secondary source 125 and the error sensor 115. When d(n) and y(n) are combined, the residual error is e(n) is substantially equal to zero for perfect cancellation, and non-zero for imperfect cancellation.

In some implementations, the filter coefficients of the adaptive filter 310 can be updated based on an adaptive process implemented using an active noise control engine 320. The active noise control engine 320 can be implemented using one or more processing devices such as a DSP, microcontroller, or microprocessor, and can be configured to update the coefficients of the adaptive filter 310 based on the error signal e(n) and/or the source signal x(n). In some implementations, the active noise control engine 320 can be configured to execute an adaptive process for reducing engine noise (e.g., harmonic noise) in a vehicle.

The adaptive filter 310 can include multiple adjustable coefficients. In some implementations, the adjustable coefficients (represented as a vector w, in general) can be determined by optimizing a given objective function (also referred to as a cost function) J[n]. For example, the objective function may be given by:

$$J[n]=\tfrac{1}{2}e^2[n] \quad (1)$$

where:

$$e[n]=d[n]+y[n] \quad (2)$$

An iterative optimization process can then be used to optimize the objective function. For example, assuming w to represent the coefficients of a finite impulse response (FIR) filter, the adaptive filter can be represented as:

$$w[n]=w[n-1]-\mu\cdot\nabla_w J[n] \quad (3)$$

and an iterative minimization process (steepest descent) can be used to solve for:

$$\min_w J[n]$$

Here, μ represents a scalar quantity for step size, i.e., a variable controlling how much the coefficients are adjusted towards the destination in each iteration, and $\nabla_w$ denotes the gradient operator. The solution to the above can be finite and unique due to a convex nature of the underlying function. In contrast, if the adaptive filter can be represented as:

$$w[n]=w[n-1]+\mu\cdot\nabla_w J[n] \quad (4)$$

the iterative maximization process (steepest ascent) would need to solve for:

$$\max_w J[n]$$

for which there may not exist a finite solution.

For illustrative purposes, the description below uses examples of a two-tap filter with coefficients $w_0$ and $w_1$. Higher order filters may also be implemented using the techniques described herein. For the two-tap filter, the time varying coefficients $w_0$ and $w_1$ can be represented as:

$$w_0[n]=w_0[n-1]-\mu\cdot e[n]\cdot\tilde{x}_i[n] \quad (5)$$

$$w_1[n]=w_1[n-1]-\mu\cdot e[n]\cdot\tilde{x}_q[n] \quad (6)$$

where $$\tilde{x}_i[n]=x_i[n]*s[n] \quad (7)$$

$$\tilde{x}_q[n]=x_q[n]*s[n] \quad (8)$$

represent orthogonal basis functions for x(n), as processed by the secondary path impulse response s[n], and μ represents a scalar quantity for step size, i.e., a variable controlling how much the coefficients are adjusted towards the destination in each iteration. Specifically, the in-phase and quadrature phase components of x[n] are given by:

$$x_i[n]=A_{ref}\cos(\omega_0 n) \quad (9)$$

and $$x_q[n]=A_{ref}\sin(\omega_0 n) \quad (10)$$

respectively, and $\omega_0$ is the frequency of x(n) (e.g., frequency of the noise generated by the engine of a vehicle).

Figure 4A:
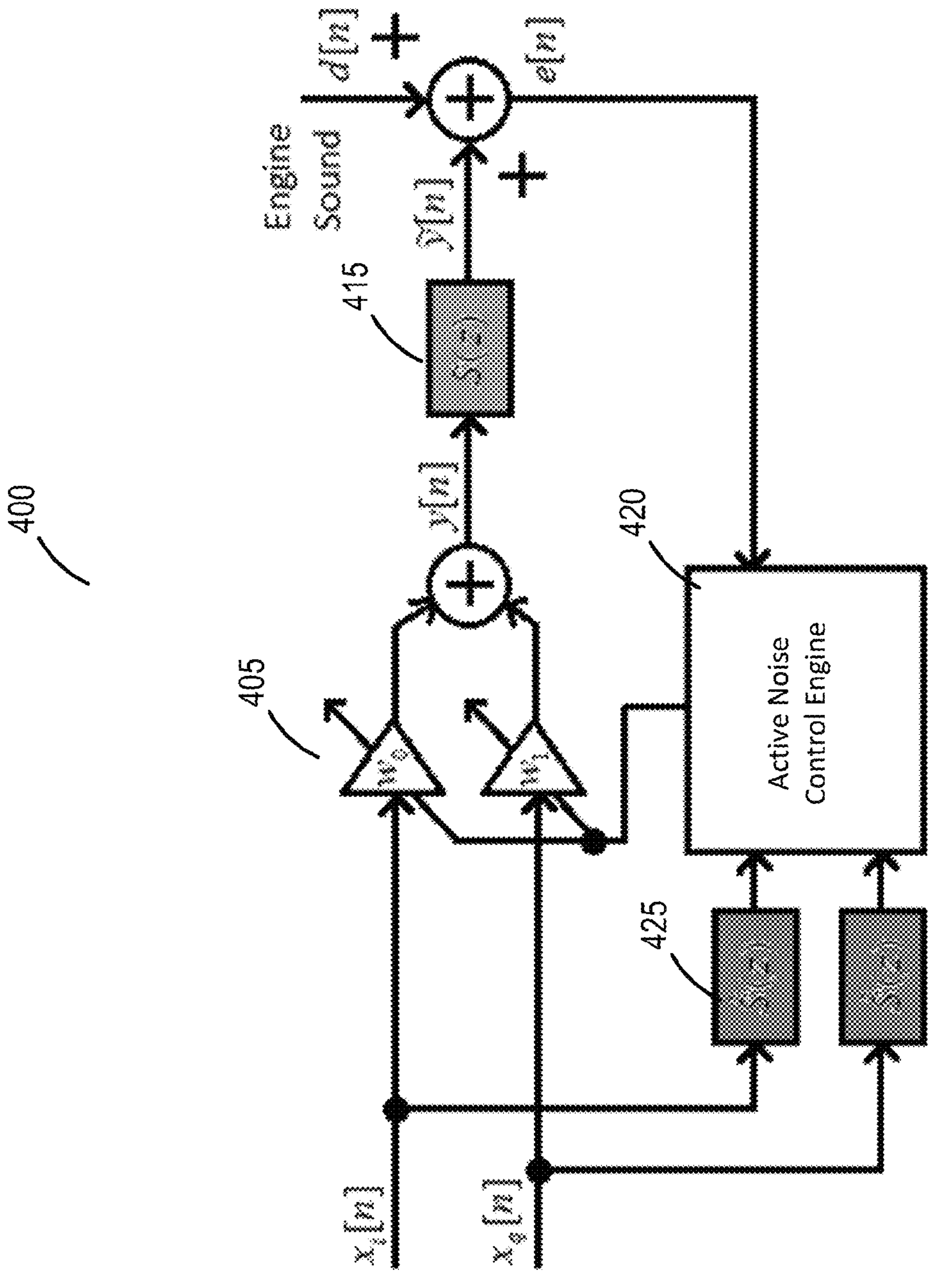
FIGS. 4A and 4B are block diagrams of example adaptive filters within an ANC system.

In some implementations, where characteristics of the secondary path are unknown, an estimated version of s[n] (denoted as $\hat{s}[n]$) may also be used. Such a signal can be represented in the time and frequency domain as:

$$\hat{S}(z)\leftrightarrow\hat{s}[n]$$

where, $\hat{S}(z)$ is the corresponding z domain representation. In such cases, the in-phase and quadrature components of the input signal can be represented as:

$$\tilde{x}_i[n]=x_i[n]*\hat{s}[n] \quad (11)$$

and $$\tilde{x}_q[n]=x_q[n]*\hat{s}[n] \quad (12)$$

respectively. This is represented in FIG. 4A, which shows an ANC system 400 with a two-tap adaptive filter 405. The active noise control engine 420 (which can be the same as or substantially similar to the active noise control engine 320 of FIG. 3) can be used to update the filter taps of the adaptive filter 405 in accordance with magnitude and phase changes in the secondary path 415. This can be done, for example, by determining an estimate 425 of the secondary path transfer function. The output of the system 400 can be represented as:

$$y[n]=w_0[n-1]\cdot x_i[n]+w_1[n-1]\cdot x_q[n] \quad (13)$$

and the residual error is given by:

$$e[n]=d[n]+y[n]*s[n] \quad (14)$$

In some implementations, if the transfer function of a secondary path S(z) varies significantly from the estimated $\hat{S}(z)$ (e.g., in one or both of magnitude and phase), the filter system may go unstable. For example, if the phase mismatch exceeds a threshold condition (e.g., ±90°), the system will be rendered unstable. Such mismatches can occur due to, for example, changes in temperatures, acoustic enclosures, placement or removal of objects in acoustic paths, etc. over time. One way of accounting for various different conditions affecting the magnitude/phase of the secondary path transfer functions is to make measurements under the various possible conditions, and estimate the transfer functions using such measurements. However, in some cases, performing such measurements in a supervised learning process can be both time consuming and expensive. For example, when designing an ANC system for a new vehicle (e.g., a model that is not commercially available yet), the supervised process described above may require procurement of a pre-production model from the vehicle manufacturer. If the manufacturer has a limited number of such pre-production models, such a procurement may be expensive. Even if such a pre-production model is procured, the ANC system designer may not be able to retain it for a long enough time period that allows the designer to make measurements for the various different conditions. In some cases, it may also not be possible to simulate all the different conditions that may affect the secondary path transfer functions in the ANC system.

Figure 4B:
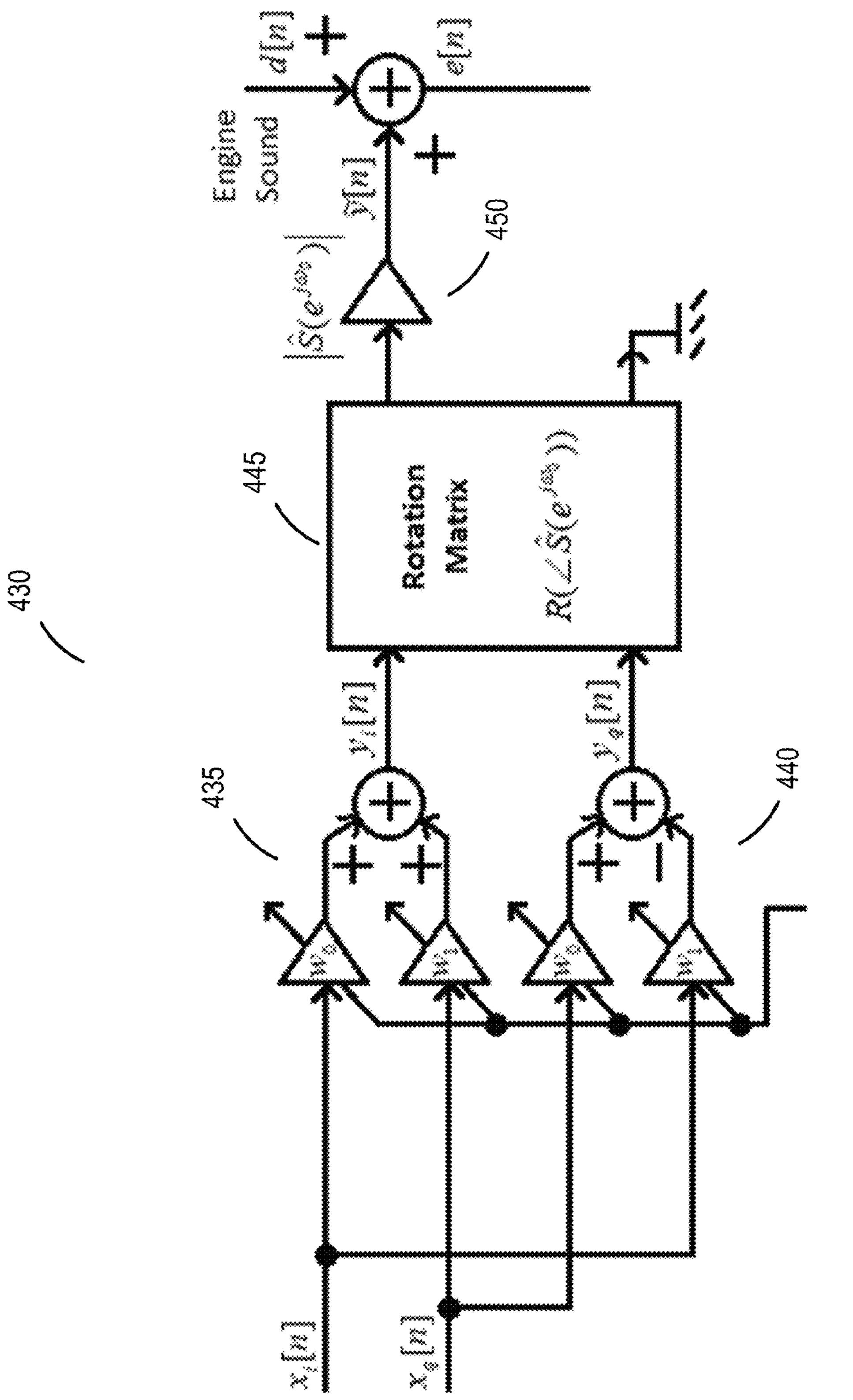

In some implementations, a supervised learning process can be avoided by determining the filter coefficients of the adaptive filter via an unsupervised learning process. For example, the phase and/or magnitude changes in one or more secondary paths may be estimated based on run-time measurements only, thereby obviating, or at least reducing the need for a priori measurements for modeling the secondary path transfer functions. This is illustrated using FIG. 4B, which shows another example of an adaptive filter within an ANC system 430. As shown in FIG. 4B, a two-tap filter each (denoted as 435 and 440, respectively) processes the in-phase and quadrature phase components of the input signal (denoted as $x_i[n]$ and $x_q[n]$, respectively). The effect of the secondary path (in a steady state) can be represented, for example, via a rotation and a gain (denoting the phase and magnitude, respectively, of the secondary path transfer function). Such an ANC system is non-intrusive in the sense that the system does not introduce any additional noise in order to measure the unknown secondary path transfer function.

In some implementations, the rotation is implemented, for example, via circuitry 445 configured to implement a rotation matrix, and the gain may be introduced, for example, using a multiplier 450. The rotation matrix can be represented, for example, as a function of an instantaneous phase angle θ as:

$$R(\theta) = \begin{bmatrix} \cos(\theta) & -\sin(\theta) \\ \sin(\theta) & \cos(\theta) \end{bmatrix} \tag{15}$$

The output can therefore be represented as:

$$\tilde{y}[n] = y[n] * s[n] \rightarrow \tilde{y}[n] = \begin{bmatrix} 1 & 0 \end{bmatrix} R(\varphi[n-1]) \begin{bmatrix} y_i[n] \\ y_q[n] \end{bmatrix} \tag{16}$$

where φ[n−1] represents the unknown phase of the secondary path. The inputs to the rotation matrix circuitry is given by:

$$y_i[n] = w_0[n-1] \cdot x_i[n] + w_1[n-1] \cdot x_q[n] \tag{17}$$

and $$y_q[n] = w_0[n-1] \cdot x_q[n] - w_1[n-1] \cdot x_i[n] \tag{18}$$

such that:

$$\tilde{y}[n] = y[n] * s[n] \tag{19}$$

$$\rightarrow \tilde{y}[n] = \begin{bmatrix} 1 & 0 \end{bmatrix} R(\varphi[n-1]) \begin{bmatrix} y_i[n] \\ y_q[n] \end{bmatrix} \tag{20}$$

$$\rightarrow \tilde{y}[n] = [\cos(\varphi[n-1]) \cdot w_0[n-1] + \sin(\varphi[n-1]) \cdot w_1[n-1]] \cdot x_i[n] + [-\sin(\varphi[n-1]) \cdot w_0[n-1] + \cos(\varphi[n-1]) \cdot w_1[n-1]] \cdot x_q[n] \tag{21}$$

where ỹ[n] represents the effect of the secondary path in the steady state.

In some implementations, the quantity φ[n−1] can be estimated, for example, based on the assumption that:

$$\theta[n-1] = \phi[n-1] \tag{22}$$

The partial derivatives within the gradient function of equation (3) can therefore be computed as:

$$\frac{\partial J[n]}{\partial w_0} = e[n] \cdot \hat{x}_i[n],\ \hat{x}_i[n] = [\cos(\theta[n-1]) \cdot x_i[n] - \sin(\theta[n-1]) \cdot x_q[n]] \tag{23}$$

$$\frac{\partial J[n]}{\partial w_1} = e[n] \cdot \hat{x}_q[n],\quad \hat{x}_q[n] = [\sin(\theta[n-1]) \cdot x_i[n] + \cos(\theta[n-1]) \cdot x_q[n]] \tag{24}$$

Therefore, by using equations (23) and (24), the updates to the adaptive filter coefficients can be estimated as a function of θ[n−1] rather than experimental measurements of the phase φ of the secondary path transfer function. The partial derivative with respect to θ can be measured as:

$$\frac{\partial J[n]}{\partial \theta} = e[n] \cdot \hat{y}_i[n] \tag{25}$$

where $$\hat{y}_i[n] = \cos\left(\theta[n-1] + \frac{\pi}{2}\right) \cdot y_i[n] - \sin\left(\theta[n-1] + \frac{\pi}{2}\right) \cdot y_q[n] \tag{26}$$

Using the equations described above, the filter taps of the two-tap filter can be updated as:

$$w_0[n] = w_0[n-1] - \mu \cdot e[n] \cdot \hat{x}_i[n] \tag{27}$$

$$w_1[n] = w_1[n-1] - \mu \cdot e[n] \cdot \hat{x}_q[n] \tag{28}$$

The instantaneous phase is also updated as:

$$\theta[n] = \theta[n-1] + \hat{\mu} \cdot e[n] \cdot \hat{y}_i[n] \tag{29}$$

Equations (27)-(29) illustrate that the filter taps are updated using steepest descent processes, and the instantaneous phase is updated using a steepest ascent process. However, other types of updates, including the case where the instantaneous phase is updated using a steepest descent process, are also within the scope of this disclosure.

In some implementations, updating the instantaneous phase can include processing the updated instantaneous phase using a non-linear function. Such a function can include one or more components. For example, the instantaneous function may be determined as:

$$\theta[n] = f(\theta[n-1] + g(\hat{\mu} \cdot e[n] \cdot \hat{y}_i[n])) \tag{30}$$

Figure 5:
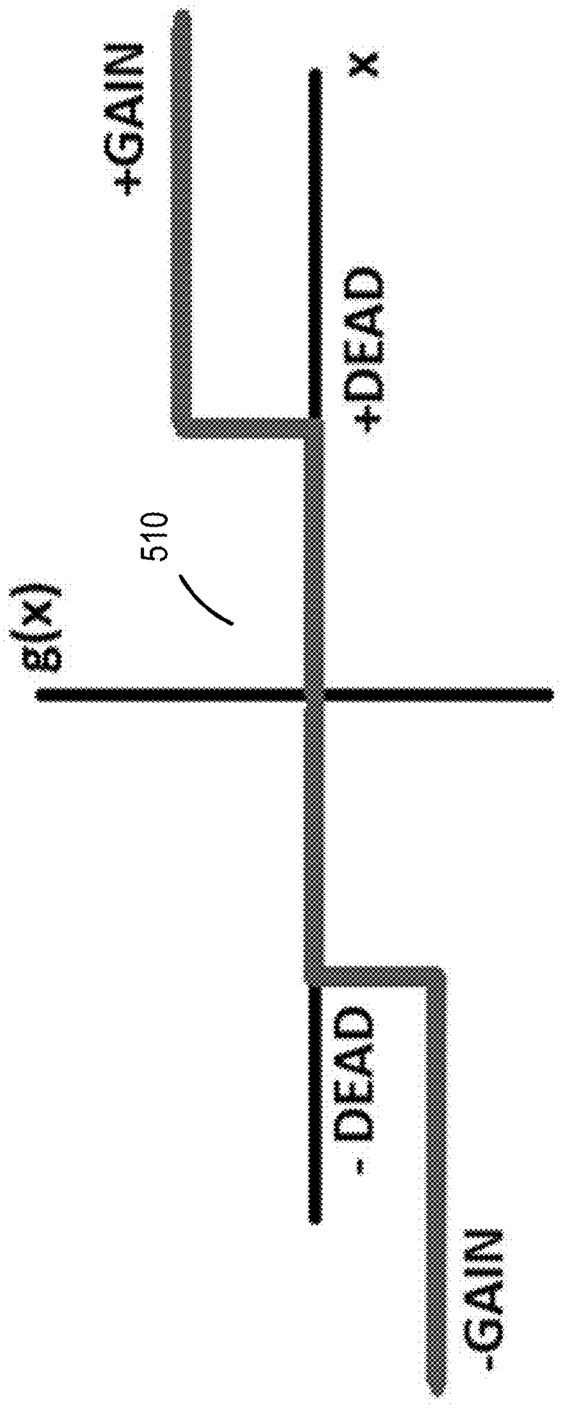
FIG. 5 is an example of function used for implementing noise resilience.

In this example, a first component (e.g., the function $f(.)$) wraps the instantaneous phase value within a predetermined range (e.g., [−π, +π]), and a second component such as the function g(.) can be used, for example, to implement a sign-like function. An example of such a function g(.) is depicted in FIG. 5. The function can include a dead zone 510 (represented in FIG. 5 as the zone between the thresholds +dead and −dead), such that the output does not change for input values in that zone. This can be used, for example, to facilitate noise resilience, and prevent the adaptive filter taps to be changed for small amounts of changes in the instantaneous phase. The thresholds (e.g., +dead and −dead) and/or the amount of output gain outside of the dead zone can be determined, for example, experimentally, or based on historical knowledge about system performance. Other functions for phase adaptation may also be used. For example, g(x)=sign (x)*x^2 can be used in place of the function depicted in FIG. 5

Figure 6:
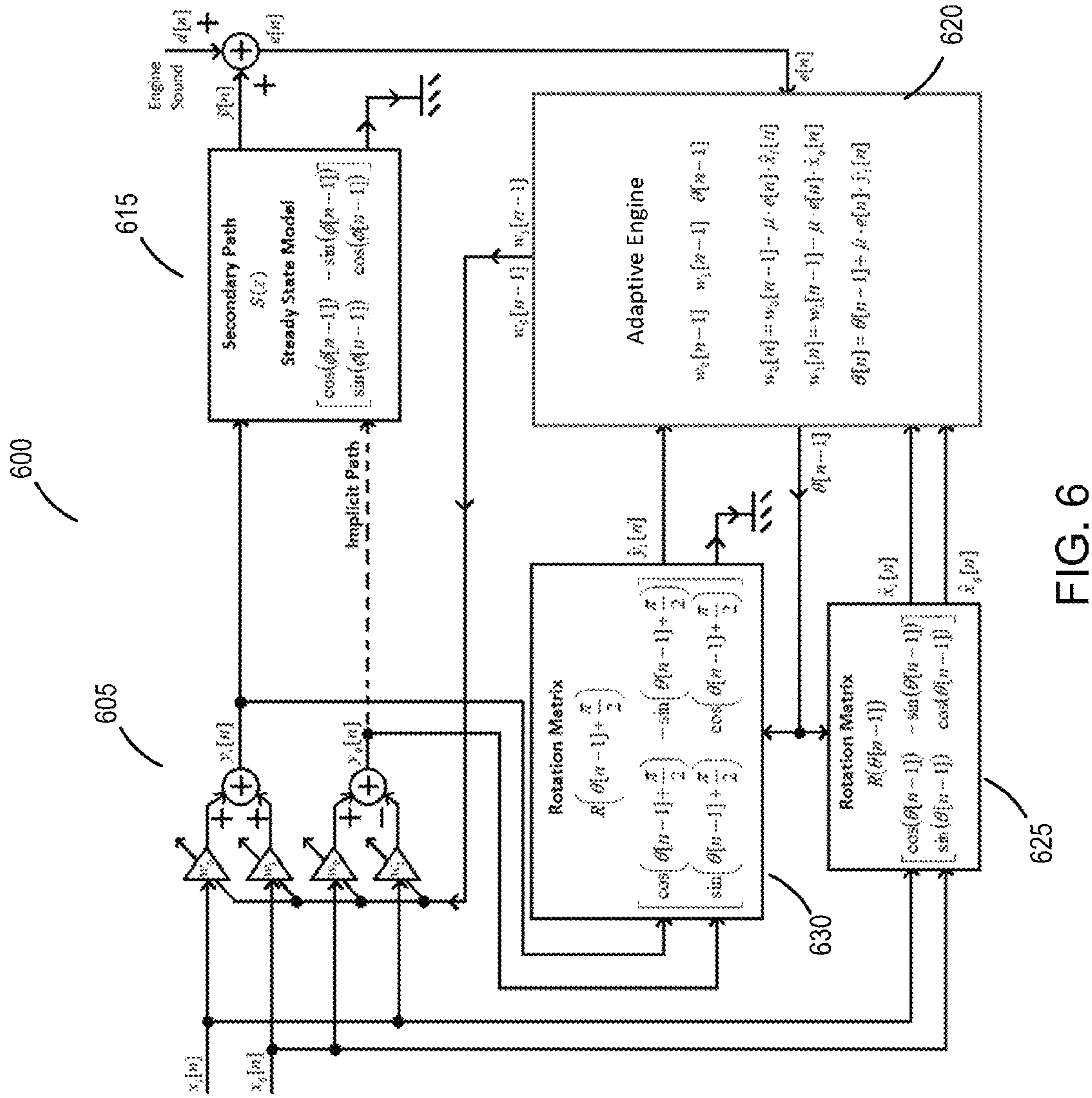
FIG. 6 is a block diagram of an example ANC system that accounts for phase changes of one or more secondary paths.

FIG. 6 shows an example ANC system 600 in accordance with the phase update process described above. The system 600 includes an adaptive filter 605, the taps for which are updated by an active noise control engine 620 based on the input signal, and one or more previous values of estimated instantaneous phase θ[n−1]. In some implementations, the system 600 includes circuitry 625 that implements a rotation matrix R(θ[n−1]). The circuitry 625 processes the in-phase and quadrature phase components of the input signal to provide the values $\hat{x}_i[n]$ and $\hat{x}_q[n]$ to the active noise control engine 620. In some implementations, the system 600 further includes circuitry 630 that implements another rotation matrix $$R\left(\theta[n-1]+\frac{\pi}{2}\right)$$

to process in-phase and quadrature components of the output of the adaptive filter 605. In some implementations, the circuitries 625 and 630 can be configured to implement the same rotation matrix. The active noise control engine 620 can be configured to update the filter coefficients and the estimate of instantaneous phase based on outputs provided by the circuitries 625 and 630, as well as the error signal e[n]. In some implementations, the active noise control engine 620 updates the filter coefficients and instantaneous phase based on equations (27)-(29).

In some implementations, the system 600 can also be operated without any updates to the instantaneous phase. For example, when operating in an acoustic environment where the secondary path transfer function does not change significantly, the phase update can be bypassed by initializing θ[n]=0. In another example, when operating in an acoustic environment where the secondary path transfer function does not change significantly, the phase update process can be configured such that the instantaneous phase remains constant over multiple updates. Therefore, the instantaneous phase update process described herein may be operated in conjunction with an existing adaptive filter, possibly on an as-needed basis. For example, the active noise control engine 620 can be configured to use the instantaneous phase updates in updating the filter coefficients only upon determining that the changes in the secondary path transfer function phase is above a threshold (which may indicate instability).

While the example in FIG. 6 shows the updates for a single secondary path and a single frequency $\omega_0$, the system can be scaled for multiple frequencies. For example, θ[n] can be stored for measurements for various frequencies (e.g., multiple engine harmonics), for example, as an array, and used in updating corresponding adaptive filters.

The phase update process described above may be used with or without updates to the magnitudes of the secondary path transfer functions. For example, the phase-update process described above may be used in conjunction with a magnitude-update process described below. The phase-update process may also be used without updates to instantaneous magnitudes of the transfer function. For example, when the magnitude changes are less than a threshold amount (e.g., approximately 20 dB or less), the phase-update process described above may be effectively used in an ANC system. In some implementations, the process may use an approximate estimate of the magnitude response of the secondary path transfer function.

Figure 7A:
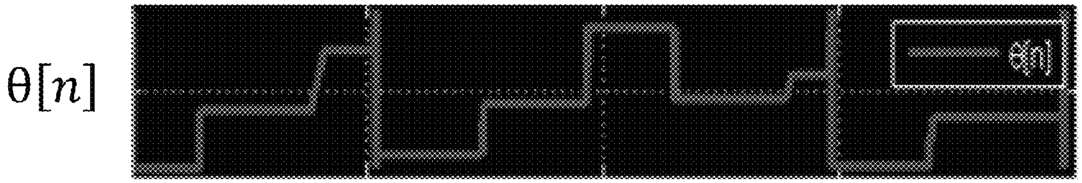
FIGS. 7A-7B show plots that illustrate the effect of accounting for secondary path phase changes.
Figure 7B:
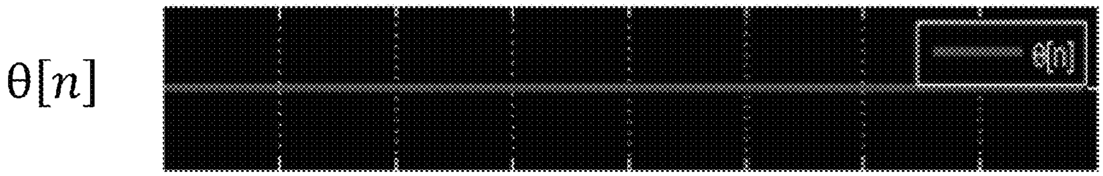

FIGS. 7A and 7B show plots that illustrate the effect of updating filter coefficients for secondary path phase changes using the techniques described above. In particular FIG. 7A illustrates the variation in θ[n] over time for a system that does not use phase-updates. FIG. 7B shows the variation in θ[n] over time for a system that uses phase-updates. As evident from FIGS. 7A and 7B, the variation in θ[n] is significantly reduced by using the phase-updates.

Figure 8A:
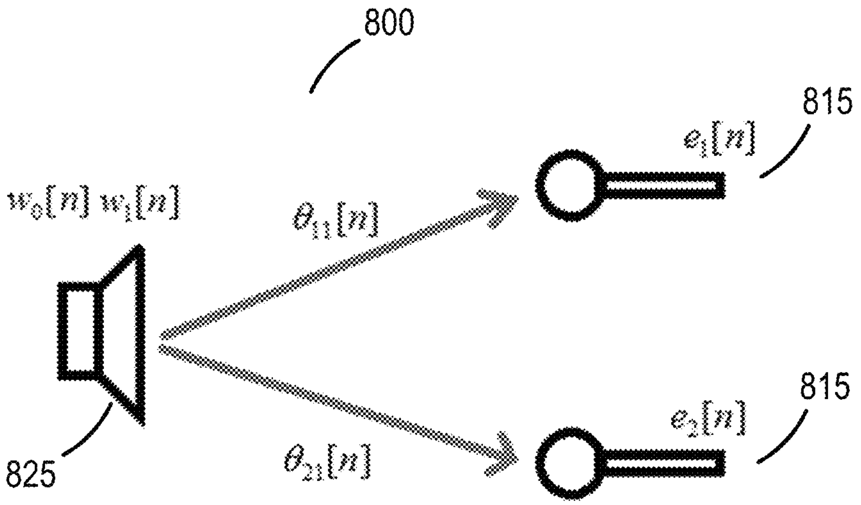
FIGS. 8A and 8B show examples of an overdetermined system and an underdetermined system, respectively, in the context of ANC systems.
Figure 8B:
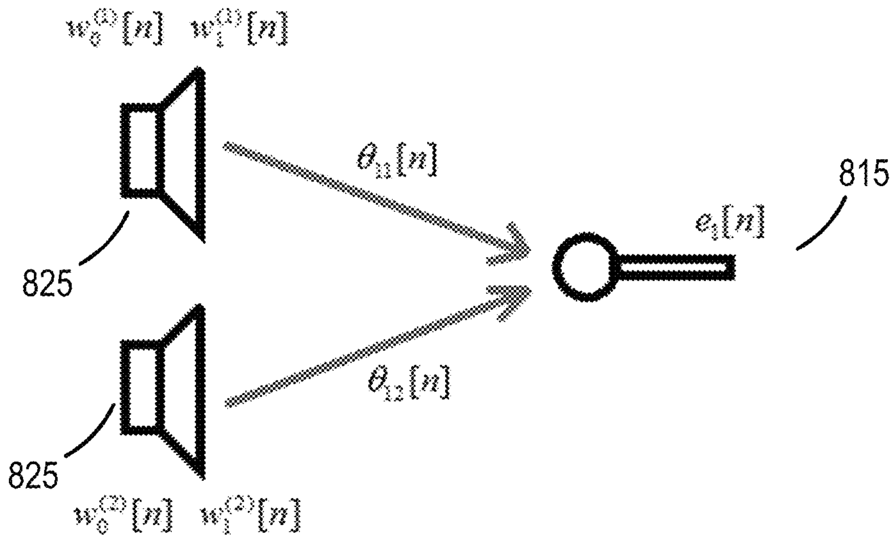

The systems described above have been illustrated primarily using examples with a single secondary path. Such systems may be referred to as Single-Input-Single-Output (SISO) systems. However, the technology can also be scaled for use in systems that include multiple secondary paths that may be formed between multiple secondary sources 125 (described in FIG. 1) and/or multiple errors sensors 115 (described in FIG. 1). In such cases, the systems may be characterized as Multiple-Input-Multiple-Output (MIMO) systems. Examples of such systems are depicted in FIGS. 8A and 8B. In particular, FIG. 8A shows an example of an overdetermined system, i.e. a system in which the number of error sensors 815 (M) is greater than the number of secondary sources 825 (L). In the example of FIG. 8A, M=2, and L=1. In this example, there are two separate secondary paths that are each characterized by a corresponding time-dependent phase θ[n]. In general, a secondary path between an error sensor i and a secondary source j may be characterized by a time-dependent phase $\theta_{ij}[n]$. Following this representation, for the example of FIG. 8A, equation (1) can be represented as:

$$J[n]:=J[w_0,w_1,\theta_{11},\theta_{21};n]=\tfrac{1}{2}(\beta_1\cdot e_1^2[n]+\beta_2\cdot e_2^2[n]) \tag{31}$$

where $\beta_{1,2}\in[0,1]$, $\beta_1+\beta_2=1$. The filter-tap updates for this example is given by:

$$w_0[n]=w_0[n-1]-\mu\cdot[\beta_1\cdot e_1[n]\cdot\hat{x}_i^{(1)}[n]+\beta_2\cdot e_2[n]\cdot\hat{x}_i^{(2)}[n]] \tag{32}$$

$$w_1[n]=w_1[n-1]-\mu\cdot[\beta_1\cdot e_1[n]\cdot\hat{x}_q^{(1)}[n]+\beta_2\cdot e_2[n]\cdot\hat{x}_q^{(2)}[n]] \tag{33}$$

The phase updates for the secondary paths can be derived to be:

$$\theta_{11}[n]=\theta_{11}[n-1]+\hat{\mu}\cdot[\beta_1\cdot e_1[n]\cdot\hat{y}_i^{(1)}[n]] \tag{34}$$

$$\theta_{21}[n]=\theta_{21}[n-1]+\hat{\mu}\cdot[\beta_2\cdot e_2[n]\cdot\hat{y}_i^{(2)}[n]] \tag{35}$$

For a more general overdetermined system with M error sensors and L=1 secondary source or speaker, the update equations can be derived using the following equations:

$$\theta_{m1}[n]=\theta_{m1}[n-1]+\hat{\mu}\cdot[\beta_m\cdot e_m[n]\cdot\hat{y}_i^{(m1)}[n]];\ m=1,2,\ldots,M \tag{36}$$

$$e_m[n]=d_m[n]+y_{m1}[n],\ \beta_m\in[0,1],\ \Sigma_{m=1}^{M}\beta_m=1 \tag{37}$$

-continued $$\hat{y}_i^{(m1)}[n] = \cos\left(\theta_{m1}[n-1] + \frac{\pi}{2}\right)\cdot y_i[n] - \sin\left(\theta_{m1}[n-1] + \frac{\pi}{2}\right)\cdot y_q[n] \quad (38)$$

$$y_i[n] = w_0^{(1)}[n-1]\cdot x_i[n] + w_1^{(1)}[n-1]\cdot x_q[n] \quad (39)$$

$$y_q[n] = w_0^{(1)}[n-1]\cdot x_q[n] - w_1^{(1)}[n-1]\cdot x_i[n] \quad (40)$$

$$w_0^{(1)}[n] = w_0^{(1)}[n-1] - \mu\cdot[\Sigma_{m=1}^{M}\beta_m\cdot e_m[n]\cdot \hat{x}_i^{(m1)}[n]] \quad (41)$$

$$w_1^{(1)}[n] = w_1^{(1)}[n-1] - \mu\cdot[\Sigma_{m=1}^{M}\beta_m\cdot e_m[n]\cdot \hat{x}_q^{(m1)}[n]] \quad (42)$$

$$\hat{x}_i^{(m1)}[n] = \cos(\theta_{m1}[n-1])\cdot x_i[n] - \sin(\theta_{m1}[n-1])\cdot x_q[n] \quad (43)$$

$$\hat{x}_q^{(m1)}[n] = \sin(\theta_{m1}[n-1])\cdot x_i[n] + \cos(\theta_{m1}[n-1])\cdot x_q[n] \quad (44)$$

FIG. 8B shows an example of an underdetermined system, e.g., a system in which the number of error sensors 815 (M) is smaller than the number of secondary sources 825 (L). In the example of FIG. 8B, M=1, and L=2. In this example too, there are two separate secondary paths that are each characterized by a corresponding time-dependent phase θ[n]. In some implementations, each secondary source or speaker device may be associated with a corresponding adaptive filter. Using the two-tap filter example, the filter taps associated with a secondary source k can be represented as $[w_0^{(k)}, w_1^{(k)}]$. Following this representation, for the example of FIG. 8B, equation (1) can be represented as:

$$J[n]:=J[w_0^{(1)},w_1^{(1)},w_0^{(2)},w_1^{(2)},\theta_{11},\theta_{12};n]=\tfrac{1}{2}e_1^2[n] \quad (45)$$

The update equations for the case can be derived to be:

$$w_0^{(1)}[n]=w_0^{(1)}[n-1]-\mu\cdot[e_1[n]\cdot\hat{x}_i^{(11)}[n]] \quad (46)$$

$$w_1^{(1)}[n]=w_1^{(1)}[n-1]-\mu\cdot[e_1[n]\cdot\hat{x}_q^{(11)}[n]] \quad (47)$$

$$w_0^{(2)}[n]=w_0^{(2)}[n-1]-\mu\cdot[e_1[n]\cdot\hat{x}_i^{(12)}[n]] \quad (48)$$

$$w_1^{(2)}[n]=w_1^{(2)}[n-1]-\mu\cdot[e_1[n]\cdot\hat{x}_q^{(12)}[n]] \quad (49)$$

$$\theta_{11}[n]=\theta_{11}[n-1]-\hat{\mu}\cdot[e_1[n]\cdot\hat{y}_i^{(11)}[n]] \quad (50)$$

$$\theta_{12}[n]=\theta_{12}[n-1]-\hat{\mu}\cdot[e_1[n]\cdot\hat{y}_i^{(12)}[n]] \quad (51)$$

For a more general underdetermined system with M=1 error sensor and L secondary sources or speakers, the update equations can be derived using the following equations:

$$\theta_{1l}[n] = \theta_{1l}[n-1] + \hat{\mu}\cdot\left[e_1[n]\cdot\hat{y}_i^{(1l)}[n]\right];\ l=1,2,\ldots,L \quad (52)$$

$$e_1[n] = d_1[n] + \Sigma_{l=1}^{L} y_{1l}[n] \quad (53)$$

$$\hat{y}_i^{(1l)}[n] = \cos\left(\theta_{1l}[n-1] + \frac{\pi}{2}\right)\cdot y_i^{(l)}[n] - \sin\left(\theta_{1l}[n-1] + \frac{\pi}{2}\right)\cdot y_q^{(l)}[n] \quad (54]$$

$$y_i^{(l)}[n] = w_0^{(l)}[n-1]\cdot x_i[n] + w_1^{(l)}[n-1]\cdot x_q[n] \quad (55)$$

$$y_q^{(l)}[n] = w_0^{(l)}[n-1]\cdot x_q[n] - w_1^{(l)}[n-1]\cdot x_i[n] \quad (55)$$

$$w_0^{(l)}[n] = w_0^{(l)}[n-1] - \mu\cdot\left[e_1[n]\cdot\hat{x}_i^{(1l)}[n]\right] \quad (56)$$

$$w_1^{(l)}[n] = w_1^{(l)}[n-1] - \mu\cdot\left[e_1[n]\cdot\hat{x}_q^{(1l)}[n]\right] \quad (57)$$

$$\hat{x}_i^{(1l)}[n] = \cos(\theta_{1l}[n-1])\cdot x_i[n] - \sin(\theta_{1l}[n-1])\cdot x_q[n] \quad (58)$$

$$\hat{x}_q^{(1l)}[n] = \sin(\theta_{1l}[n-1])\cdot x_i[n] + \cos(\theta_{1l}[n-1])\cdot x_q[n] \quad (59)$$

For the general case of M error sensors and L secondary sources, a total of (2×L+L×M) update equations are needed. These can be derived to be:

$$\theta_{ml}[n] = \theta_{ml}[n-1] + \hat{\mu}\cdot\left[\beta_m\cdot e_m[n]\cdot\hat{y}_i^{(ml)}[n]\right] \quad (60)$$

$$m=1,2,\ldots,M;\ l=1,2,\ldots,L$$

$$e_m[n] = d_m[n] + \Sigma_{l=1}^{L} y_{ml}[n],\ \beta_m\in[0,1],\ \Sigma_{m=1}^{M}\beta_m = 1 \quad (61)$$

$$\hat{y}_i^{(ml)}[n] = \cos\left(\theta_{ml}[n-1] + \frac{\pi}{2}\right)\cdot y_i^{(l)}[n] - \sin\left(\theta_{ml}[n-1] + \frac{\pi}{2}\right)\cdot y_q^{(l)}[n] \quad (62)$$

$$y_i^{(l)}[n] = w_0^{(l)}[n-1]\cdot x_i[n] + w_1^{(l)}[n-1]\cdot x_q[n] \quad (63)$$

$$y_q^{(l)}[n] = w_0^{(l)}[n-1]\cdot x_q[n] + w_1^{(l)}[n-1]\cdot x_i[n] \quad (64)$$

$$w_0^{(l)}[n] = w_0^{(l)}[n-1] - \mu\cdot\left[\Sigma_{m=1}^{M}\beta_m\cdot e_m[n]\cdot\hat{x}_i^{(ml)}[n]\right] \quad (65)$$

$$w_1^{(l)}[n] = w_1^{(l)}[n-1] - \mu\cdot\left[\Sigma_{m=1}^{M}\beta_m\cdot e_m[n]\cdot\hat{x}_q^{(ml)}[n]\right] \quad (66)$$

$$\hat{x}_i^{(ml)}[n] = \cos(\theta_{ml}[n-1])\cdot x_i[n] - \sin(\theta_{ml}[n-1])\cdot x_q[n] \quad (67]$$

$$\hat{x}_q^{(ml)}[n] = \sin(\theta_{ml}[n-1])\cdot x_i[n] + \cos(\theta_{ml}[n-1])\cdot x_q[n] \quad (68)$$

The ANC systems described above function based on adaptively updating one or more phase estimates of the secondary path transfer function(s). In some implementations, estimates of secondary path transfer function magnitudes can be updated, which in turn may improve noise cancellation performance and/or improve convergence speed. For example, in MIMO systems, the relative balance of secondary path magnitudes can affect an eigenvalue spread (conditioning) of the system, and thus affect performance. In some implementations, modeled secondary path transfer function magnitudes may also function as a step-size variable, and therefore affect convergence rates. For example, when used in conjunction with phase update techniques described above, the magnitude update techniques may, in some cases, improve the convergence rate of the corresponding ANC systems.

The magnitude update techniques can be used in conjunction with the phase update techniques described above, or independent of any phase update technique. For example, in situations where the secondary path transfer function phase does not change significantly, or an approximate characterization of the phase changes is available, the magnitude update techniques can be used without any phase updates.

Figure 9A:
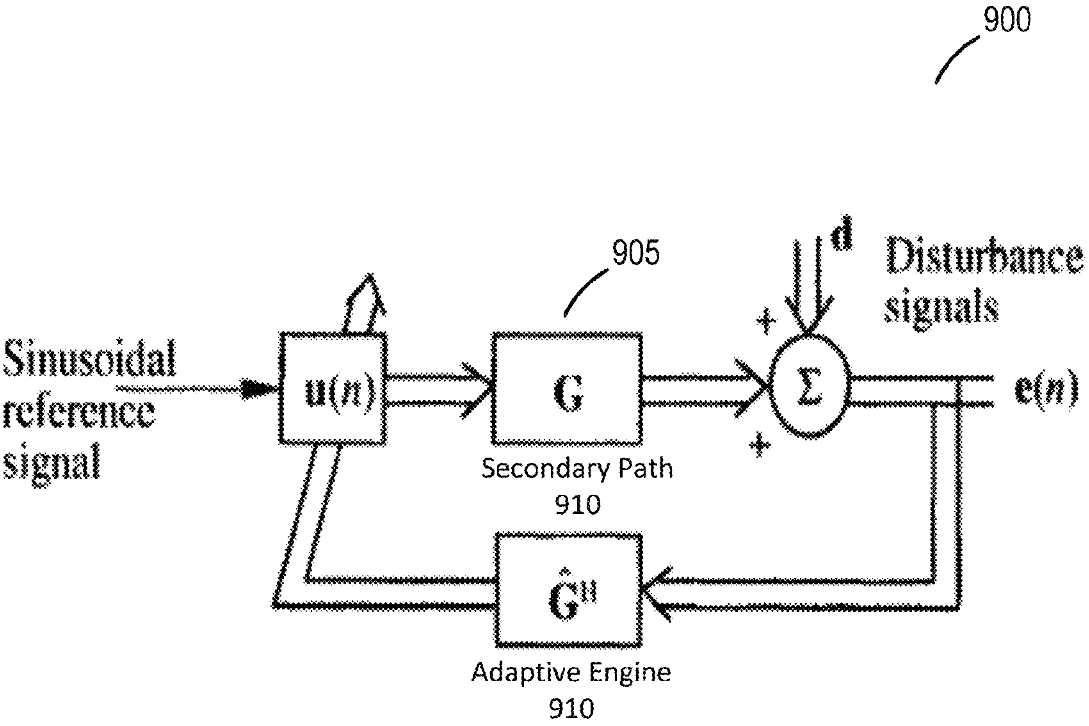
FIGS. 9A and 9B are block diagrams of an example of an alternative representation of an ANC system.
Figure 9B:
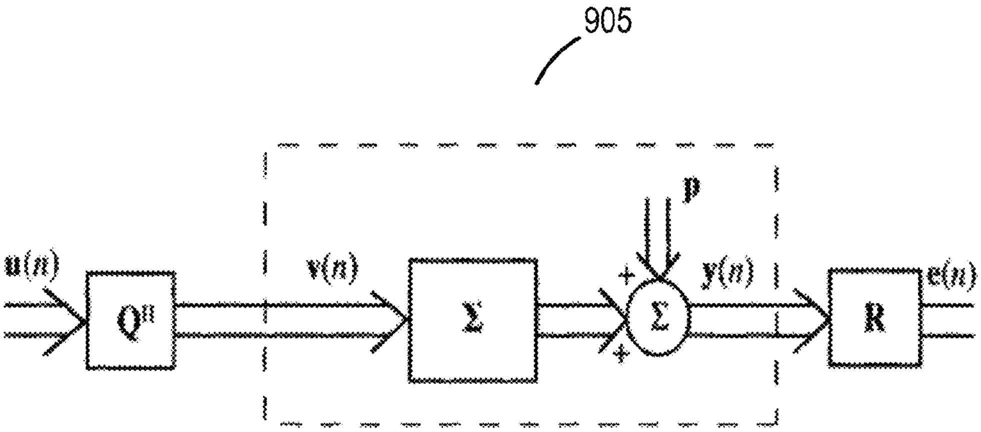

FIG. 9 shows a block diagram of an example of an alternative representation 900 of an ANC system. The representation 900 can be used for an eigenvalue analysis on a stability and convergence speed of the corresponding system. In the example of FIG. 9, a transfer function representing a secondary path 905 can be denoted as G, and the active noise control engine 910 models the secondary path transfer function as Ĝ. In this example, the secondary path 905 represents a collection of secondary paths in a MIMO system, and therefore denoted as a matrix. The secondary path transfer function G may be orthogonalized, for example, using singular decomposition, as:

$$G=R\Sigma Q^H \quad (69)$$

where R is a real or complex unitary matrix, Σ is a rectangular diagonal matrix with non-negative real numbers on the diagonal, and $Q^H$ (the Hermetian of Q, or simply the transpose of Q if Q is real) is a real or complex unitary matrix. This representation is depicted in FIG. 9B. The diagonal entries $\Sigma_{m,m}$ of Σ are known as the singular values of G. The eigenvalues of a perfectly modeled system are the singular values of the matrix Σ, squared, given by:

$$\lambda_m=(\Sigma(m,m))^2 \tag{70}$$

In some implementations, approximations to the eigenvalues may be calculated from the matrices G and Ĝ as:

$$\lambda=\text{eig}(\hat{G}\cdot G) \tag{71}$$

The disturbance vector d can be projected into the principal component space as:

$$p=R^H d \tag{72}$$

where each entry in the vector p (denoted by $p_m$) represents a particular mode of disturbance. Using equations (69)-(71), equation (1) can be reduced to:

$$J(n) \approx J_{min} + \sum_{m=1}^{M} |p_m|^2 e^{-2\alpha\lambda_m n} \tag{73}$$

where Jmin represents a minimum amount of noise in the system, and a represents a modal step size. Equation (73) shows that the eigenvalues $\lambda_m$ control the rate of cancellation for each mode of the disturbance, $p_m$.

The convergence of an adaptive filter in an ANC system may depend on a spread of the eigenvalues. For example, a wider spread of the eigenvalues may result in slower convergence towards steady state error. In some implementations, knowledge of the secondary path transfer function(s) allows for reducing the spread of the eigenvalues. In some implementations, where prior knowledge about the secondary path transfer function(s) is not available, relative secondary path magnitudes for each secondary source (e.g., speaker device) may be inferred based on a rate of change of the filter-coefficients of the corresponding adaptive filter. For example, if the filter-taps are all initialized as equal, in the absence of any prior knowledge of the secondary path magnitudes, the secondary path that changes the most may generate the largest changes in the filter-coefficients. Therefore, by measuring the changes in adaptive filter coefficients, magnitude changes in the corresponding secondary path transfer functions may be estimated, and such estimates may be used in determining future weights for the adaptive filter.

In some implementations, time-dependent instantaneous differences in filter weights can be measured as:

$$\delta(n)=\text{abs}[w(n)-w(n-1)] \tag{74}$$

where w(n) denotes a vector of filter weights at a particular time. For L secondary sources, and a two-tap filter for each secondary source, δ and w have dimensions [L*2, 1]. Specifically, δ and w may be represented as:

$$\delta(n) = \begin{bmatrix} \delta_{10} \\ \delta_{11} \\ \delta_{20} \\ \delta_{21} \\ \vdots \\ \delta_{L0} \\ \delta_{L1} \end{bmatrix} \tag{75}$$

-continued $$w(n) = \begin{bmatrix} w_{10} \\ w_{11} \\ w_{20} \\ w_{21} \\ \vdots \\ w_{L0} \\ w_{L1} \end{bmatrix} \tag{76}$$

In some implementations, the instantaneous differences may be smoothed using a digital filter. For example, a single pole filter can be used to smooth the instantaneous differences as:

$$\zeta(n)=\eta*\zeta(n)+(1-\eta)*\zeta(n-1) \tag{77}$$

where η is a small value (e.g., 0.01), which may be determined, for example, empirically. In some implementations, the time-dependent differences can be inverted as:

$$\xi(n) = \frac{1}{\zeta(n)+\varepsilon} \tag{78}$$

where ϵ is a small number (e.g., $10^{-6}$) that is added to the denominator to avoid any potential division by zero. In some implementations, the inverted differences may be normalized as:

$$\Xi(n) = \frac{\xi(n)}{\sqrt{\overline{\xi(n)}^2}} \tag{79}$$

In some implementations, the normalized quantity Ξ (or the un-normalized quantity ζ) for each filter tap can be averaged to obtain a mean quantity for each adaptive filter. A separate value for each filter tap may also be used. For two-tap adaptive filters and L secondary sources, the mean quantities can be represented as:

$$\Xi(n) = \text{mean}\begin{bmatrix} \Xi_{10} & \Xi_{11} \\ \Xi_{20} & \Xi_{21} \\ \vdots & \vdots \\ \Xi_{L0} & \Xi_{L1} \end{bmatrix} = \begin{bmatrix} \Xi_1 \\ \Xi_2 \\ \vdots \\ \Xi_L \end{bmatrix} \tag{80}$$

Magnitudes of the modeled secondary path transfer function Ĝ may then be estimated based on the values of $\overline{\Xi}$(n). For example, rows from $\overline{\Xi}$(n) may be replicated across microphones to obtain estimated magnitudes of the modeled secondary path transfer function Ĝ as:

$$|\hat{G}(n)| = \begin{bmatrix} \Xi_1, \Xi_1 & \Xi_2, \Xi_2 & \dots & \Xi_L, \Xi_L \\ \Xi_1, \Xi_1 & \Xi_2, \Xi_2 & \dots & \Xi_L, \Xi_L \\ \vdots & & \ddots & \vdots \\ \Xi_1, \Xi_1 & \Xi_2, \Xi_2 & \dots & \Xi_L, \Xi_L \end{bmatrix}_{M\times 2L} \tag{81}$$

In some implementations, the estimated magnitudes of the secondary path transfer functions may be used in conjunction with phase estimates for the corresponding secondary path transfer functions. For example, the modeled secondary path transfer function $\hat{G}$ may be represented in terms of both magnitude and phase estimates as:

$$\hat{G}(n) = \begin{bmatrix} \Xi_1, \Xi_1 & \Xi_2, \Xi_2 & \ldots & \Xi_L, \Xi_L \\ \Xi_1, \Xi_1 & \Xi_2, \Xi_2 & \ldots & \Xi_L, \Xi_L \\ \vdots & & \ddots & \vdots \\ \Xi_1, \Xi_1 & \Xi_2, \Xi_2 & \ldots & \Xi_L, \Xi_L \end{bmatrix}_{M\times 2L} \circledast \theta(n) \quad (82)$$

where Θ is element-wise multiplication, and Θ(n) is given by:

$$\Theta(n) = \begin{bmatrix} \sin(2\pi ft(n)+\theta_{11}), \cos(2\pi ft(n)+\theta_{11}) & \ldots & \sin(2\pi ft(n)+\theta_{1L}), \cos(2\pi ft(n)+\theta_{1L}) \\ \sin(2\pi ft(n)+\theta_{21}), \cos(2\pi ft(n)+\theta_{21}) & \ldots & \sin(2\pi ft(n)+\theta_{2L}), \cos(2\pi ft(n)+\theta_{2L}) \\ \vdots & \ddots & \vdots \\ \sin(2\pi ft(n)+\theta_{M1}), \cos(2\pi ft(n)+\theta_{M1}) & \ldots & \sin(2\pi ft(n)+\theta_{ML}), \cos(2\pi ft(n)+\theta_{ML}) \end{bmatrix}_{M\times 2L} \quad (83)$$

The filter update equations can therefore be represented as:

$$w_{2L\times 1}(n+1)=w_{2L\times 1}(n)+\hat{G}(n)^T_{2L\times M}{}^*e_{M\times 1}(n) \quad (84)$$

Figure 10A:
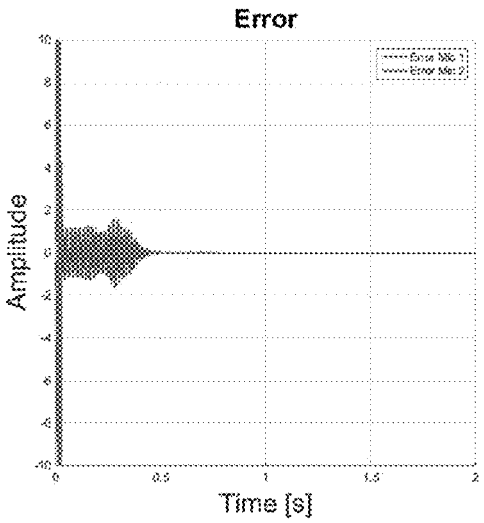
FIGS. 10A-10D show plots that illustrate the effect of estimating secondary path magnitude changes.
Figure 10B:
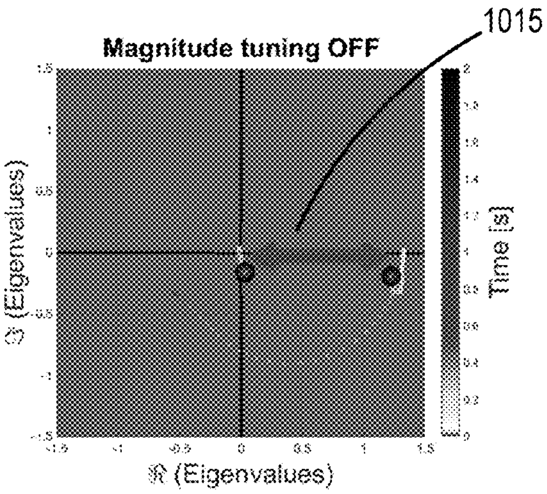
Figure 10C:
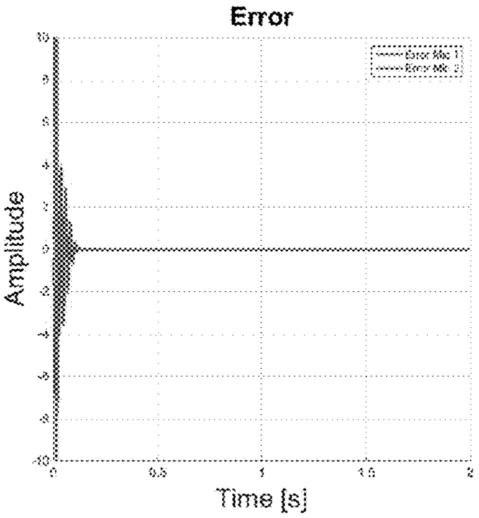
Figure 10D:
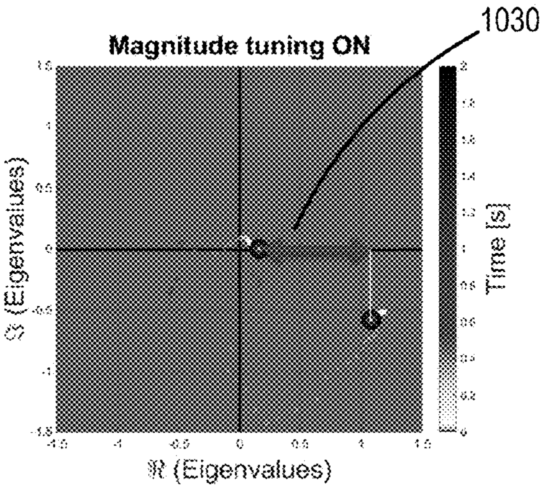

FIGS. 10A-10D illustrate examples of effects of using the magnitude update techniques described above. Specifically, FIG. 10A represents the time variance of error signals from two microphones (i.e., error sensors) in a four speaker, two microphone, MIMO ANC system when magnitude updates were not used. FIG. 10B shows the corresponding distribution of eigenvalues on the complex plane. FIGS. 10C and 10D represent the same plots, respectively, when both phase and magnitudes updates in accordance with the above description were used. FIG. 10B illustrates that when magnitude updates were not used, the spread 1015 in the real parts of the eigenvalues was moderately large, and for several eigenvalues, the real part was negative, thereby indicating a degree of instability. Using the phase updates improved the stability (as indicated by less number of eigenvalues with negative real parts in FIG. 10D), and using the magnitude updates reduced the spread 1030 (as compared to the spread 1015 in FIG. 10B) in the real parts of the eigenvalues. The reduction in spread resulted in faster convergence as illustrated in FIG. 10C.

In some cases, even after convergence filter coefficients may continue to change. This can happen, for example, if an ANC system is affected by energy outside of the frequency (or frequencies) being canceled by the ANC system. For example, in practical ANC systems, low frequency content captured by the error sensors may cause changes to the adaptive filter coefficients even after the filter has converged. Referring to equation (3) a high value for the step size μ can result in more residual error and therefore high instantaneous changes in the filter coefficients. In some implementations, the step size μ can be adaptively varied, for example, to control the changes in the adaptive filter coefficients, and therefore also the changes in the magnitude updates.

Figure 11:
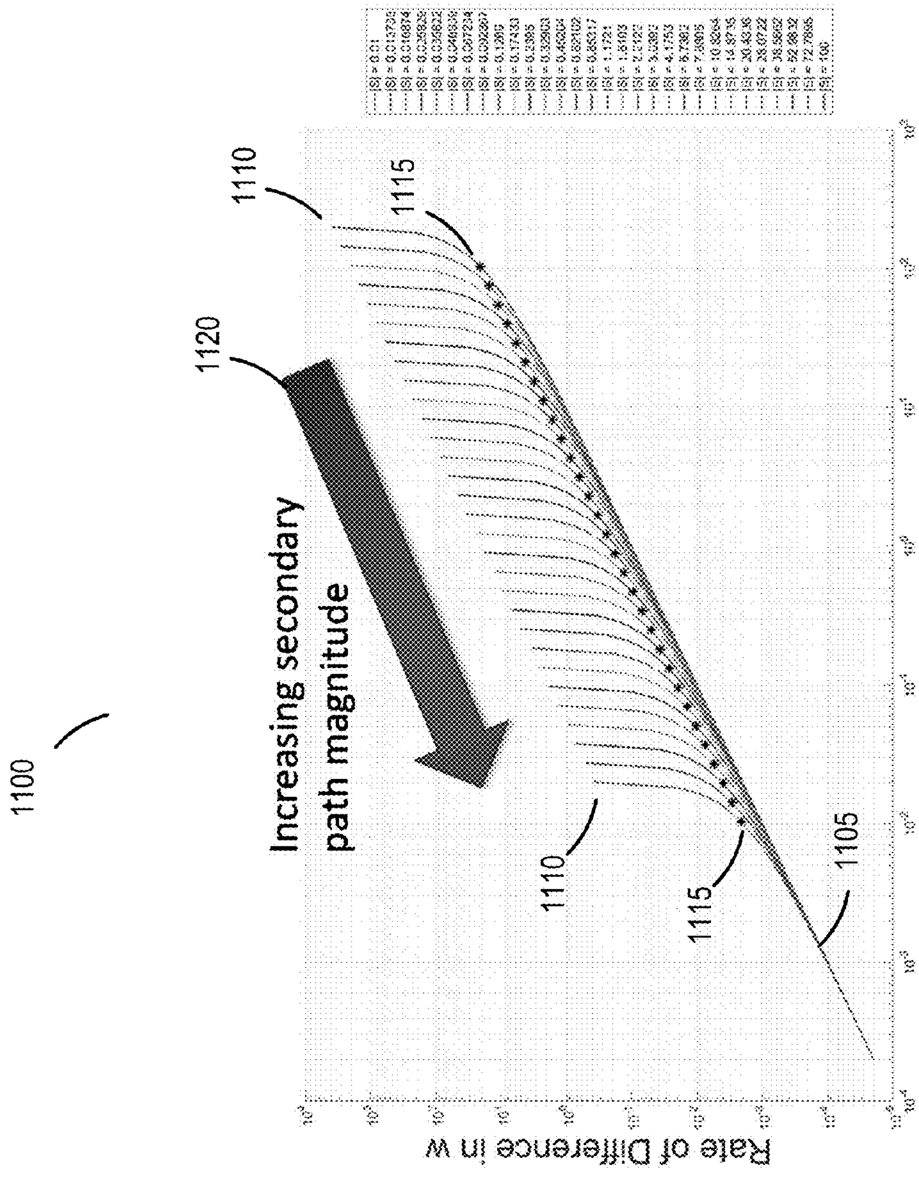
FIG. 11 shows a plot that illustrates the rate of change in filter coefficients as a function of step size for various magnitudes of secondary path transfer function.

FIG. 11 shows an example plot 1100 that illustrates the relationship between the rate of instantaneous differences of the adaptive filter coefficients w, the step-size μ, and the magnitude of the secondary path transfer function, which is denoted in this example as |S|. Each curve in plot 1100 shows how the rate of instantaneous differences in filter coefficients varies as a function of μ for a fixed secondary path magnitude. As illustrated by the portion 1105 of the curves, the rate difference is substantially same for all secondary path magnitudes for low values of μ. The upper boundaries 1110 of each curve represents a point where the corresponding system becomes unstable. The black asterisks 1115 represent substantially optimal values of μ for corresponding secondary path magnitudes. An optimal value can represent, for example, the theoretical step size that can be used for a perfect cancellation in one time-step with a magnitude-normalized step size of one. The direction of increasing secondary path magnitudes is shown using the arrow 1120.

Figure 12:
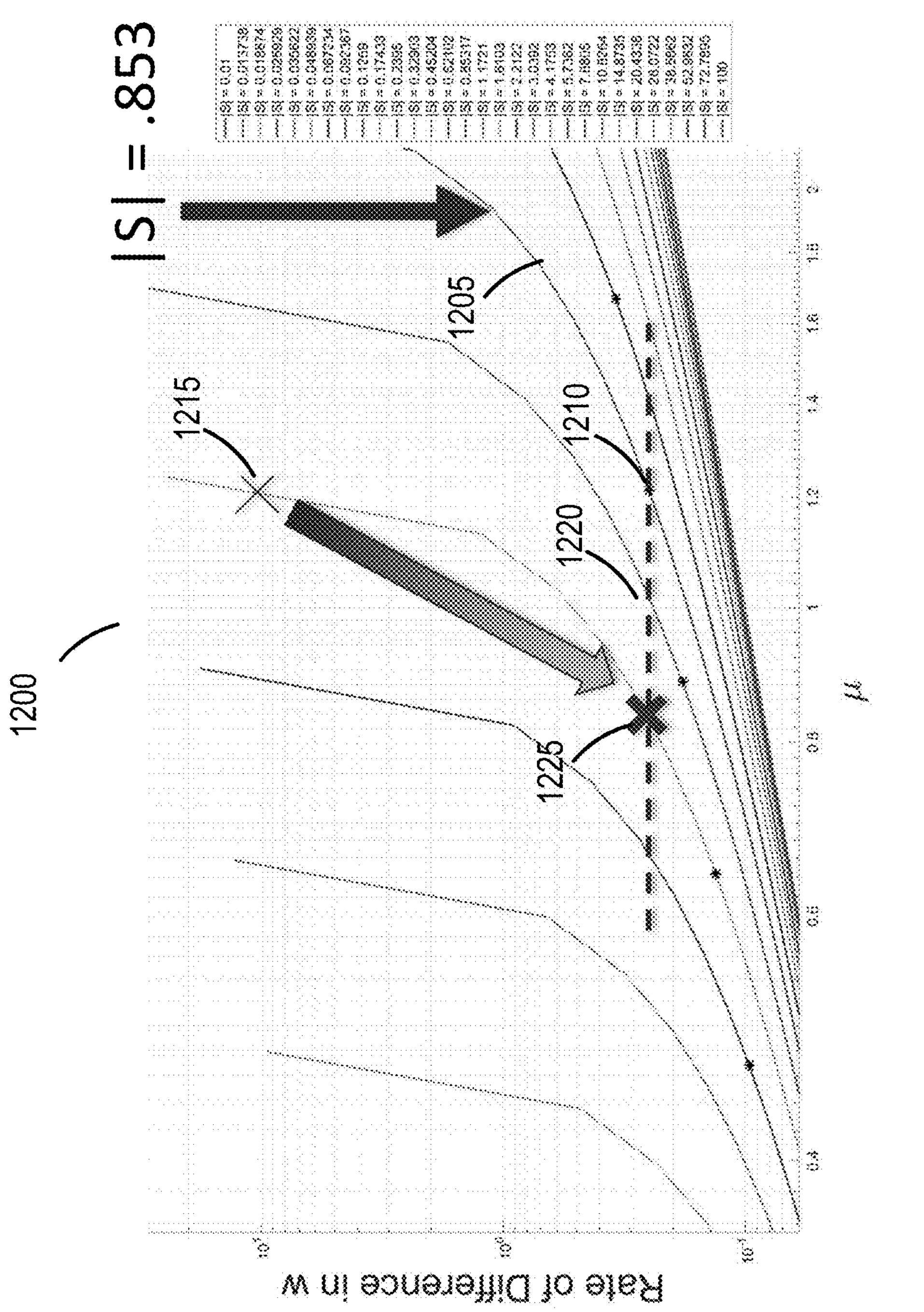
FIG. 12 is a magnified portion of the plot of FIG. 11, with additional annotations to illustrate the process of adaptively adjusting the step size in accordance with changes to the secondary path magnitude.

FIG. 12 shows a magnified portion 1200 of the plot 1100. As such, the example in FIG. 12 illustrates the process of adaptively adjusting the step size in accordance with changes to the secondary path magnitude. In this example, the initial secondary path magnitude is |S|=0.853. This corresponds to the curve 1205. The initial value for μ is the optimal value 1210 (approx. 1.2) for that secondary path magnitude, which corresponds to an instantaneous difference in filter coefficients $w_{diff}$=0.25. In this example, if |S| increases to 1.61, for an unchanged value of μ, $w_{diff}$=10. This in turn can lead to a large change in the rate of instantaneous differences in the filter coefficients. However, to maintain a substantially same $w_{diff}$ (as represented by the line 1220), the corresponding active noise control engine can be configured to adjust μ, such that μ=0.85 (represented by the point 1225).

In some implementations, the above adjustments to step size can also be performed for MIMO systems. For example, referring back to equation (77), target values for $w_{diff}$, ζ, and a margin, υ (around which no changes are made) can be set, and may be adjusted based on the target value of ζ (e.g., max(ζ(n)). This can be implemented, for example, as follows:

$$\text{If } \max(\zeta(n))<\tau-\upsilon, \mu(n)=\mu(n-1)*\kappa$$

$$\text{If } \max(\zeta(n))\geq\tau-\upsilon \text{ AND } \max(\zeta(n))\leq\tau+\upsilon, \mu(n)=\mu(n-1)$$

$$\text{If } \max(\zeta(n))>\tau+\upsilon, \mu(n)=\mu(n-1)/\kappa$$

where κ is a multiplier, and [κ, τ, υ] are initialized nominally, for example as [1.01, 0.01, 3 dB].

Figure 13B:
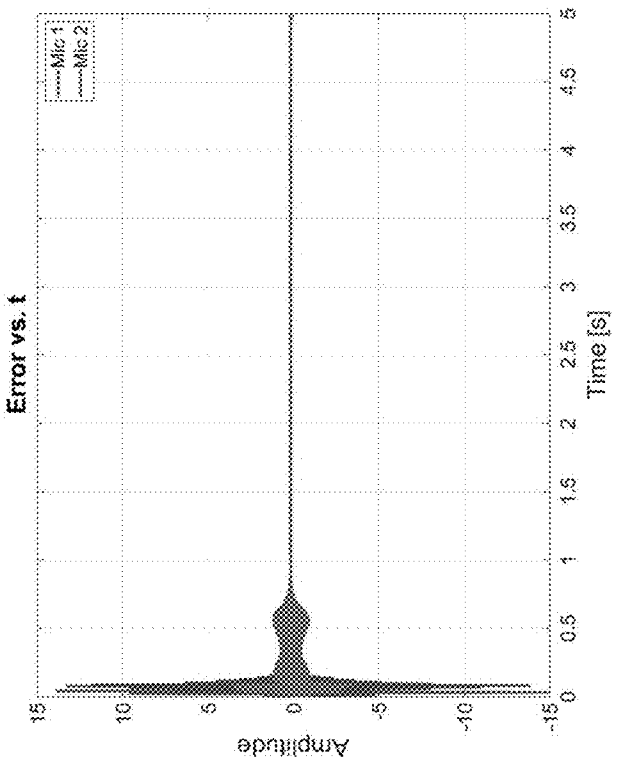
FIGS. 13A-13D show example plots that illustrate improvements in the rate of convergence of an adaptive filter by using techniques described herein.
Figure 13A:
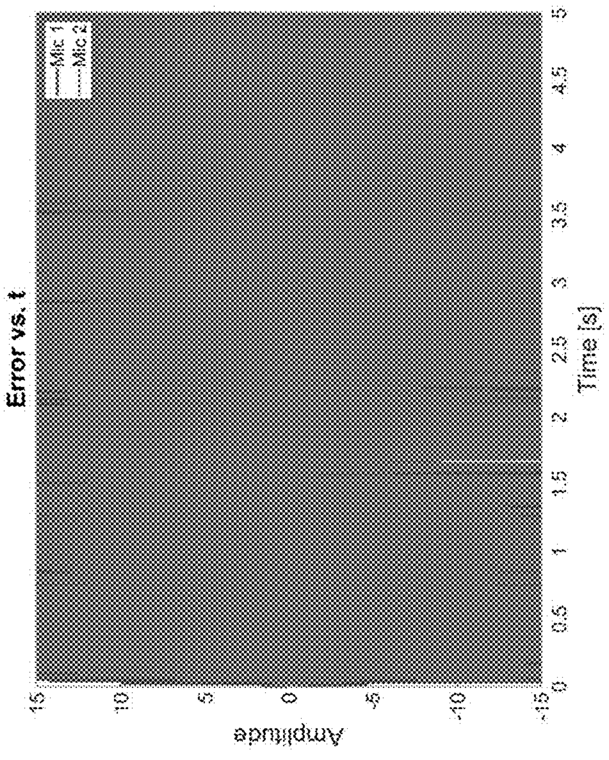
Figure 13D:
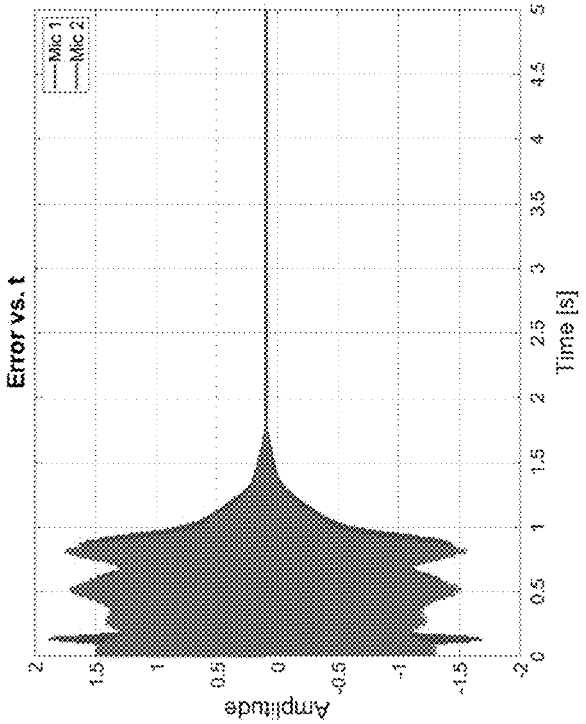
Figure 13C:
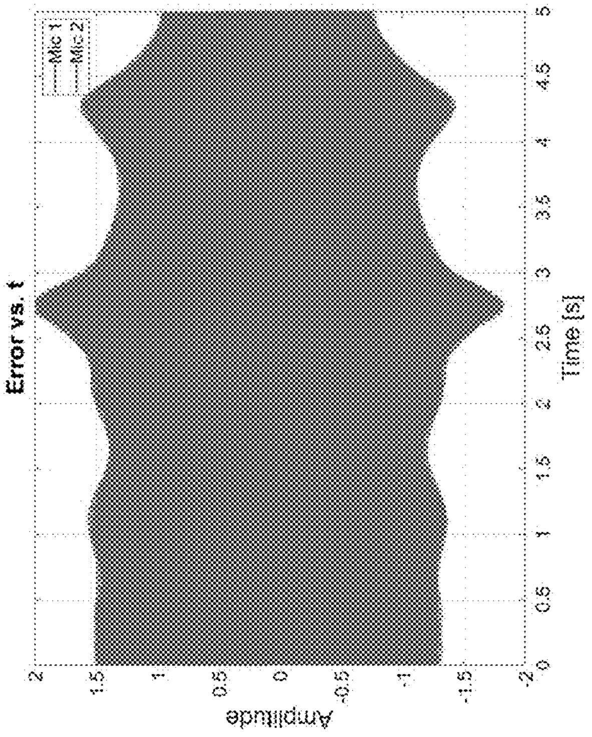

FIGS. 13A-13D show examples of the effects that may be achieved using the step size-adjusted magnitude updates as mentioned above. FIG. 13A shows the time-dependent error signal in the absence of step size-adjusted magnitude updates for high transfer function magnitudes with phase adjustments. This example is for a two-microphone case. As evident from FIG. 13A, the errors for both microphones are high and do not appear to converge. In contrast, when the step size-adjusted magnitude updates are used (FIG. 13B), fast convergence to a near-zero error is observed for both microphones. FIG. 13C shows the time-dependent error signal in the absence of step size-adjusted magnitude updates for relatively lower transfer function magnitudes. In this case too, the errors for both microphones are high and do not appear to converge within the observed timeframe. In contrast, when the step size-adjusted magnitude updates are used (FIG. 13D), fast convergence to a near-zero error is observed for both microphones.

Figure 14:
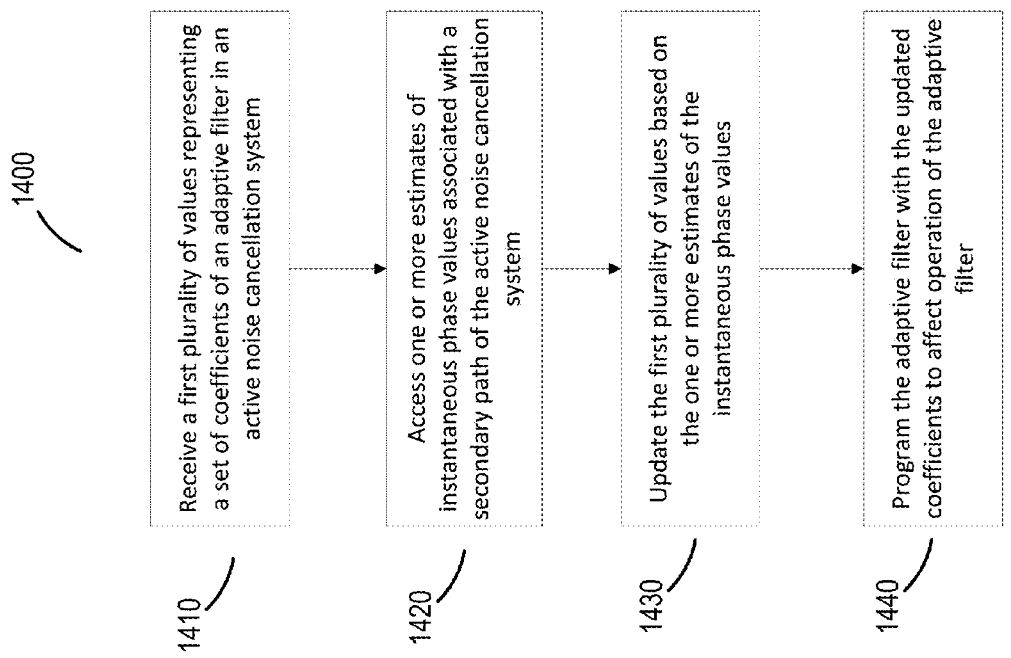
FIG. 14 is a flowchart of an example process for programming an adaptive filter based on phase changes in a secondary path of an ANC system.

FIG. 14 shows a flowchart for an example process 1400 for programming an adaptive filter based on phase changes in a secondary path of an ANC system. In some implementations, at least a portion of the process 1400 may be performed, for example, by an active noise control engine of an ANC system described above. Example operations of the process 1400 include receiving a first plurality of values representing a set of coefficients of an adaptive filter disposed in an ANC system (1410). For example, the first plurality of values can represent a set of coefficients of the adaptive filter at a particular time. In some implementations, the ANC system is configured to cancel a noise signal generated by an engine (e.g., a vehicle engine). For example, the adaptive filter may be deployed within an ANC system such as an ANC system for cancelling harmonic noise generated by a vehicle engine. The adaptive filter can be the same as or substantially similar to the adaptive filters 310, 405, 435, 440, or 605 described above. In some implementations, the ANC system includes one or more acoustic transducers for generating an anti-noise signal for canceling a noise signal, and one or more microphones for sensing a residual noise resulting from at least a partial cancellation of the noise signal by the anti-noise signal.

The operations also include accessing one or more estimates of instantaneous phase values associated with a transfer function representing an effect of a secondary path of the active noise cancellation system (1420). In some implementations, the secondary path may include, for example, one or more transducers that produces the anti-noise signal, one or more error sensors that measure an error signal produced as a result of an interaction between the noise signal and the anti-noise signal, and an acoustic path disposed between the one or more transducers and the one or more error sensors. The acoustic path can include a portion of an interior of an automobile. In some implementations, the transfer function may be represented as a matrix, where a given element of the matrix represents a secondary path between a particular microphone of the one or more microphones and a particular acoustic transducer of the one or more acoustic transducers.

The one or more estimates of instantaneous phase values can be generated analytically, for example, during operation of the adaptive filter, and independent of any predetermined model of the secondary path. In some implementations, the one or more estimates of instantaneous phase values can be generated using an unsupervised learning process. In some implementations, the one or estimates of instantaneous phase values are updated, and the updated estimates are made available as the one or more estimates of instantaneous phase values for subsequent iterations. In some implementations, the estimates of the instantaneous phase values may be generated, for example, as described above with reference to FIG. 6.

The operations of the process 1400 also includes updating the first plurality of values based on the one or more estimates of the instantaneous phase values to generate a set of updated coefficients for the adaptive filter (1430). This can include, for example, receiving a second plurality of values representing a signal used as a reference signal in the active noise cancellation system, and updating the first plurality of values based also on the second plurality of values. In some implementations, the second plurality values can each include one value representing an in-phase component of the reference signal, and one value representing a quadrature-phase component of the reference signal. The reference signal can be based on, for example, a noise signal generated by an engine (e.g., a vehicle engine).

In some implementations, updating the first plurality of values based on the second plurality of values can include phase-shifting the reference signal based on the one or more estimates of the instantaneous phase values associated with the transfer function, and updating the first plurality of values based on the phase-shifted reference signal. Updating the first plurality of values can also include phase-shifting an output of the adaptive filter based on the one or more estimates of the instantaneous phase values associated with the transfer function representing the effect of the secondary path, and updating the first plurality of values based also on the phase-shifted output of the adaptive filter. In some implementations, the first plurality of values can be updated based also on one or more values of instantaneous magnitudes associated with the transfer function representing the effect of the secondary path. In some implementations, the instantaneous magnitude may be determined based on a rate at which the coefficients of the adaptive filter change over time.

The operations of the process 1400 also includes programming the adaptive filter with the set of updated coefficients to affect operation of the adaptive filter (1440). The adaptive filter can be programmed such that the active noise cancellation system cancels a noise signal generated by an engine (e.g., a vehicle engine). This can be done, for example, by generating a control signal based on an output of the adaptive filter, wherein the control signal causes production of an anti-noise signal for cancelling a noise signal. A phase and magnitude of the anti-noise signal is such that the anti-noise signal reduces an effect of the noise signal. In some implementations, the control signal can be generated by phase shifting the output of the adaptive filter based on the one or more estimates of the instantaneous phase values associated with the transfer function representing the effect of the secondary path.

Figure 15:
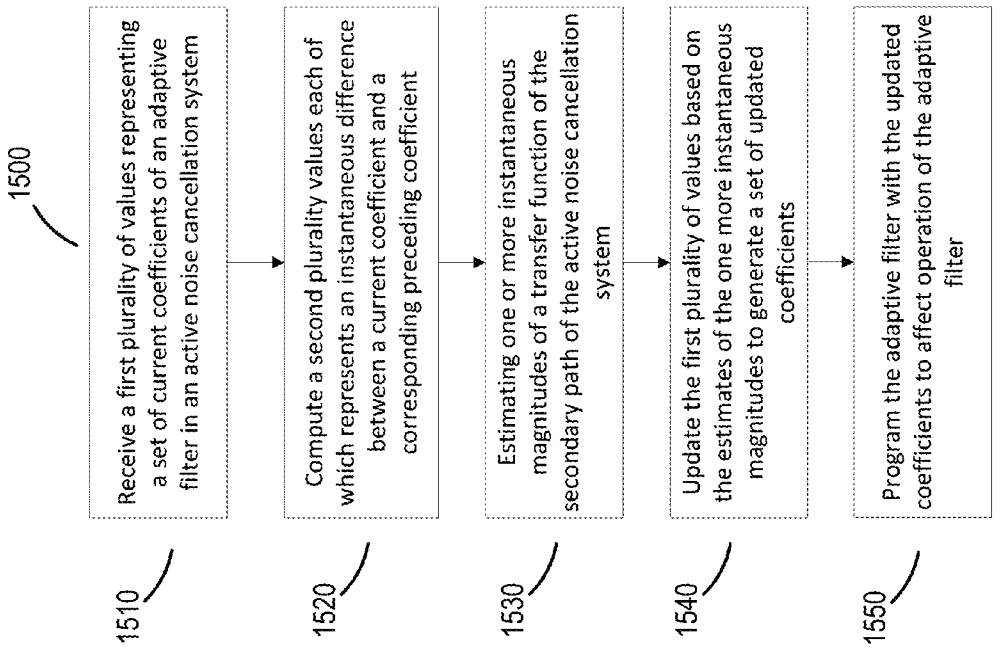
FIG. 15 is a flowchart of an example process for programming an adaptive filter based on magnitude changes in a secondary path of an ANC system.

FIG. 15 shows a flowchart for an example process 1500 for programming an adaptive filter based on magnitude changes in a secondary path of an ANC system. In some implementations, the at least a portion of the process 1500 may be performed, for example, by an active noise control engine of an ANC system described above. Example operations of the process 1500 include receiving a first plurality of values representing a set of current coefficients of an adaptive filter disposed in an ANC system (1510). The ANC system and/or adaptive filter can be the same as or substantially similar to those described with respect to FIG. 14. In some implementations, the ANC system includes one or more acoustic transducers for generating an anti-noise signal for canceling a noise signal, and one or more microphones for sensing a residual noise resulting from at least a partial cancellation of the noise signal by the anti-noise signal.

The operations of the process 1500 also include computing a second plurality of values, each of which represents an instantaneous difference between a current coefficient and a corresponding preceding coefficient of the adaptive filter (1520). In some implementations, this can be done, for example, using equation (74) described above.

The operations of the process 1500 further include estimating, based on the second plurality of values, one or more instantaneous magnitudes of a transfer function that represents an effect of a secondary path of the ANC system (1530). In some implementations, the transfer function may be represented as a matrix, wherein a given element of the matrix represents a secondary path between a particular microphone of the one or more microphones and a particular acoustic transducer of the one or more acoustic transducers.

In some implementations, the one or more instantaneous magnitudes may be estimated based on a rate at which the coefficients of the adaptive filter change over time. In some implementations, determining the one or more instantaneous magnitudes of the transfer function can include applying a digital filter on the second plurality of values, and determining the one or more instantaneous magnitudes of the transfer function based on an output of the digital filter. In some implementations, this can be done by performing one or more processes to implement equations (77)-(81) described above. For example, estimating the one or more instantaneous magnitudes of the transfer function can include determining a reciprocal of a value of the rate at which the coefficients of the adaptive filter change over time, and estimating the one or more instantaneous magnitudes of the transfer function based on the reciprocal of the value.

The operations of the process 1500 also includes updating the first plurality of values based on estimates of the one or more instantaneous magnitudes to generate a set of updated coefficients for the adaptive filter (1540). In some implementations, this can include receiving or determining one or more estimates of instantaneous phase values associated with the transfer function, and updating the first plurality of values based also on the one or more estimates of instantaneous phase values. In some implementations, the instantaneous phase values can be computed based on the process 1400 described above.

The operations of the process 1500 also include programming the adaptive filter with the set of updated coefficients to affect operation of the adaptive filter (1550). The adaptive filter can be programmed such that the active noise cancellation system cancels a noise signal generated by an engine (e.g., a vehicle engine). This can be done, for example, by generating a control signal based on an output of the adaptive filter, wherein the control signal causes production of an anti-noise signal for cancelling a noise signal. A phase and magnitude of the anti-noise signal is such that the anti-noise signal reduces an effect of the noise signal.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Other embodiments not specifically described herein are also within the scope of the following claims. Elements of different implementations described herein may be combined to form other embodiments not specifically set forth above. Elements may be left out of the structures described herein without adversely affecting their operation. Furthermore, various separate elements may be combined into one or more individual elements to perform the functions described herein

What is claimed is:

1. A computer-implemented method comprising:

receiving, at one or more processing devices, a first plurality of values representing a set of current coefficients of an adaptive filter disposed in an active noise cancellation system;

computing, by the one or more processing devices, a second plurality of values each of which represents an instantaneous difference between a current coefficient and a corresponding preceding coefficient of the adaptive filter;

estimating, based on the second plurality of values, one or more instantaneous magnitudes of a transfer function that represents an effect of a secondary path of the active noise cancellation system;

updating the first plurality of values based on estimates of the one or more instantaneous magnitudes to generate a set of updated coefficients for the adaptive filter; and programming the adaptive filter with the set of updated coefficients to affect operation of the adaptive filter.

2. The method of claim 1, wherein the one or more instantaneous magnitudes are estimated based on a rate at which the coefficients of the adaptive filter change over time.

3. The method of claim 1, wherein, determining the one or more instantaneous magnitudes of the transfer function comprises:

applying a digital filter on the second plurality of values; and determining the one or more instantaneous magnitudes of the transfer function based on an output of the digital filter.

4. The method of claim 2, wherein, estimating one or more instantaneous magnitudes of the transfer function further comprises:

determining a reciprocal of a value of the rate at which the coefficients of the adaptive filter change over time; and estimating the one or more instantaneous magnitudes of the transfer function based on the reciprocal of the value of the rate.

5. The method of claim 4, further comprising:

receiving, at the one or more processing devices, one or more estimates of instantaneous phase values associated with the transfer function; and updating the first plurality of values based also on the one or more estimates of instantaneous phase values.

6. The method of claim 5, wherein the one or more estimates of instantaneous phase values are generated analytically during an operation of the adaptive filter, and independent of any prior model of the secondary path.

7. The method of claim 5, wherein the one or more estimates of instantaneous phase values are generated using an unsupervised learning process.

8. The method of claim 1, further comprising generating a control signal based on an output of the adaptive filter, wherein the control signal causes production of an anti-noise signal configured to reduce the effect of a noise signal.

9. The method of claim 8, wherein noise signal is generated by a vehicle engine.

10. The method of claim 8, wherein the first plurality of values is updated based also on an error signal produced based on residual noise resulting from at least a partial cancellation of the noise signal by the anti-noise signal.

11. The method of claim 1, wherein the active noise cancellation system comprises one or more acoustic transducers for generating an anti-noise signal for canceling a noise signal, and one or more microphones for sensing a residual noise resulting from at least a partial cancellation of the noise signal by the anti-noise signal.

12. The method of claim 11, further comprising representing the transfer function as a matrix, wherein a given element of the matrix represents a secondary path between a particular microphone of the one or more microphones and a particular acoustic transducer of the one or more acoustic transducers.

13. A system comprising:

an active noise control engine including one or more processing devices configured to:

receive a first plurality of values representing a set of current coefficients of an adaptive filter disposed in an active noise cancellation system;

compute a second plurality of values each of which represents an instantaneous difference between a current coefficient and a corresponding preceding coefficient of the adaptive filter;

estimate, based on the second plurality of values, one or more instantaneous magnitudes of a transfer function that represents an effect of a secondary path of the active noise cancellation system;

update the first plurality of values based on estimates of the one or more instantaneous magnitudes to generate a set of updated coefficients for the adaptive filter; and program the adaptive filter with the set of updated coefficients to affect operation of the adaptive filter.

14. The system of claim 13, wherein the one or more instantaneous magnitudes are estimated based on a rate at which the coefficients of the adaptive filter change over time.

15. The system of claim 13, wherein, determining the one or more instantaneous magnitudes of the transfer function comprises:

applying a digital filter on the second plurality of values; and determining the one or more instantaneous magnitudes of the transfer function based on an output of the digital filter.

16. The system of claim 14, wherein estimating one or more instantaneous magnitudes of the transfer function further comprises:

determining a reciprocal of a value of the rate at which the coefficients of the adaptive filter change over time; and estimating the one or more instantaneous magnitudes of the transfer function based on the reciprocal of the value of the rate.

17. The system of claim 16, wherein the active noise control engine is configured to:

receive one or more estimates of instantaneous phase values associated with the transfer function; and update the first plurality of values based also on the one or more estimates of instantaneous phase values.

18. The system of claim 17, wherein the one or more estimates of instantaneous phase values are generated analytically during an operation of the adaptive filter, and independent of any prior model of the secondary path.

19. One or more machine-readable storage devices having encoded thereon computer readable instructions for causing one or more processors to perform operations comprising:

receiving a first plurality of values representing a set of current coefficients of an adaptive filter disposed in an active noise cancellation system;

computing a second plurality of values each of which represents an instantaneous difference between a current coefficient and a corresponding preceding coefficient of the adaptive filter;

estimating, based on the second plurality of values, one or more instantaneous magnitudes of a transfer function that represents an effect of a secondary path of the active noise cancellation system;

updating the first plurality of values based on estimates of the one or more instantaneous magnitudes to generate a set of updated coefficients for the adaptive filter; and programming the adaptive filter with the set of updated coefficients to affect operation of the adaptive filter.

20. The or more machine-readable storage devices of claim 19, wherein the one or more instantaneous magnitudes are estimated based on a rate at which the coefficients of the adaptive filter change over time.

* * * * *